United States Patent [19]

Anderson et al.

[11] 4,336,810

[45] Jun. 29, 1982

[54] METHOD AND APPARATUS FOR ARRHYTHMIA ANALYSIS OF ECG RECORDINGS

[75] Inventors: Donald L. Anderson, San Juan Capistrano; Isaac R. Cherry, Mission Viejo; John A. Ripley, Newport Beach; David T. Tanaka, San Juan Capistrano, all of Calif.

[73] Assignee: Del Mar Avionics, Irvine, Calif.

[21] Appl. No.: 192,192

[22] Filed: Sep. 30, 1980

[51] Int. Cl.³ .............................................. A61B 5/04
[52] U.S. Cl. .................................................. 128/702
[58] Field of Search ................ 128/702, 703, 704, 710, 128/711, 712; 360/33 ME; 364/417

[56] References Cited

U.S. PATENT DOCUMENTS

| | | | |
|---|---|---|---|
| 3,616,791 | 11/1971 | Harris | 128/702 |
| 3,654,916 | 4/1972 | Neilson | 128/702 |
| 4,073,011 | 2/1978 | Cherry et al. | 128/711 |

Primary Examiner—William E. Kamm
Attorney, Agent, or Firm—Beehler, Pavitt, Siegemund, Jagger & Martella

[57] ABSTRACT

Method and apparatus for arrhythmia analysis of Holter-type ECG recordings including a tape playback unit having an analog signal output of successive ECG complexes or heart beats, a converter for generating data composites representing each complex, a computer for making and storing data templates in bins corresponding to operator classification of complexes as normal, supraventricular ectopic (SVE), ventricular ectopic (VE), or unknown, for comparing successive composites with stored templates and conditions to determine a match condition, and for signaling a corresponding event to an event counter and display. In learn mode the computer signals the tape playback to stop and to display an unmatched complex for operator classification and possible subsequent generation of a new template, after which scanning is resumed.

40 Claims, 16 Drawing Figures

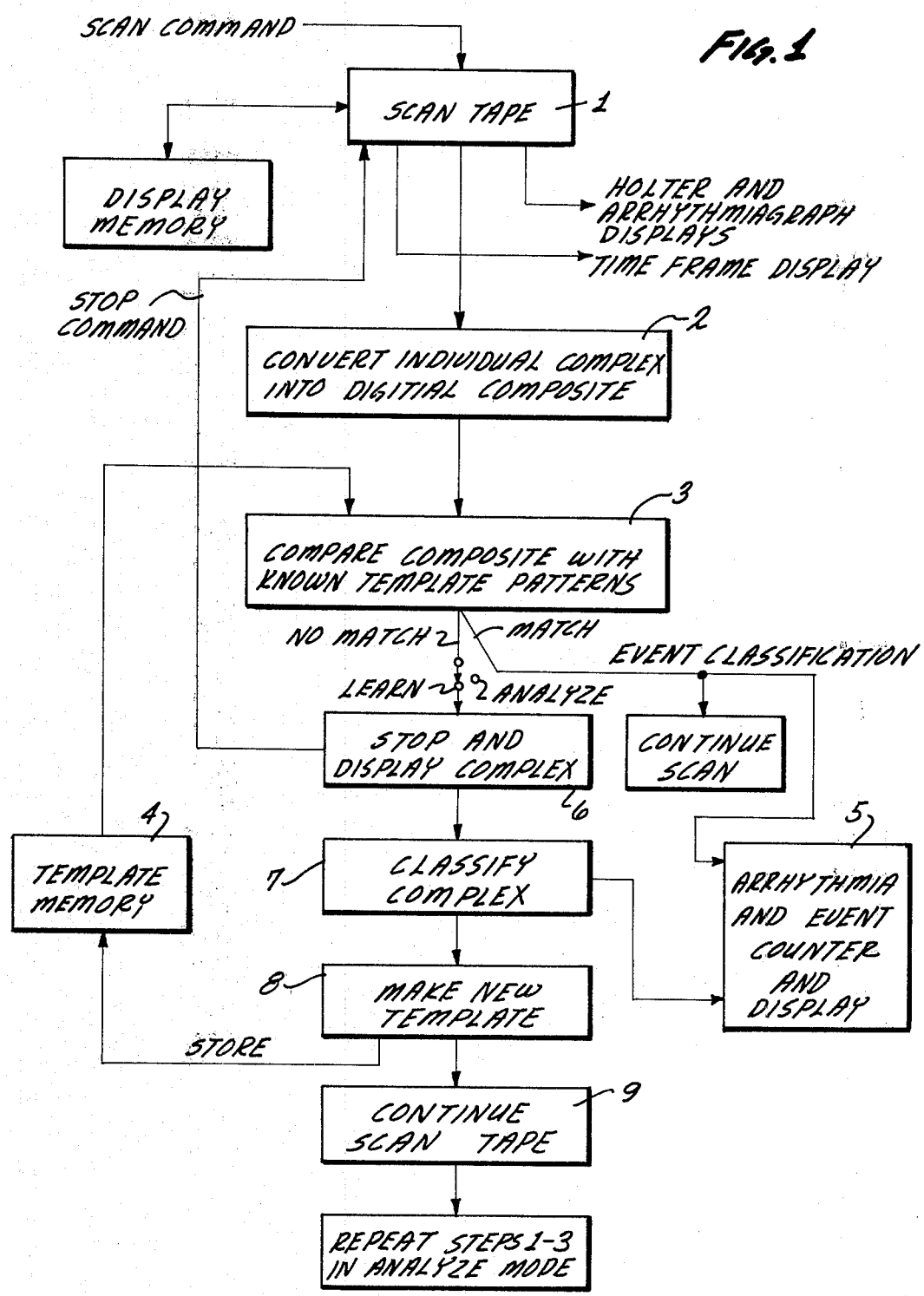

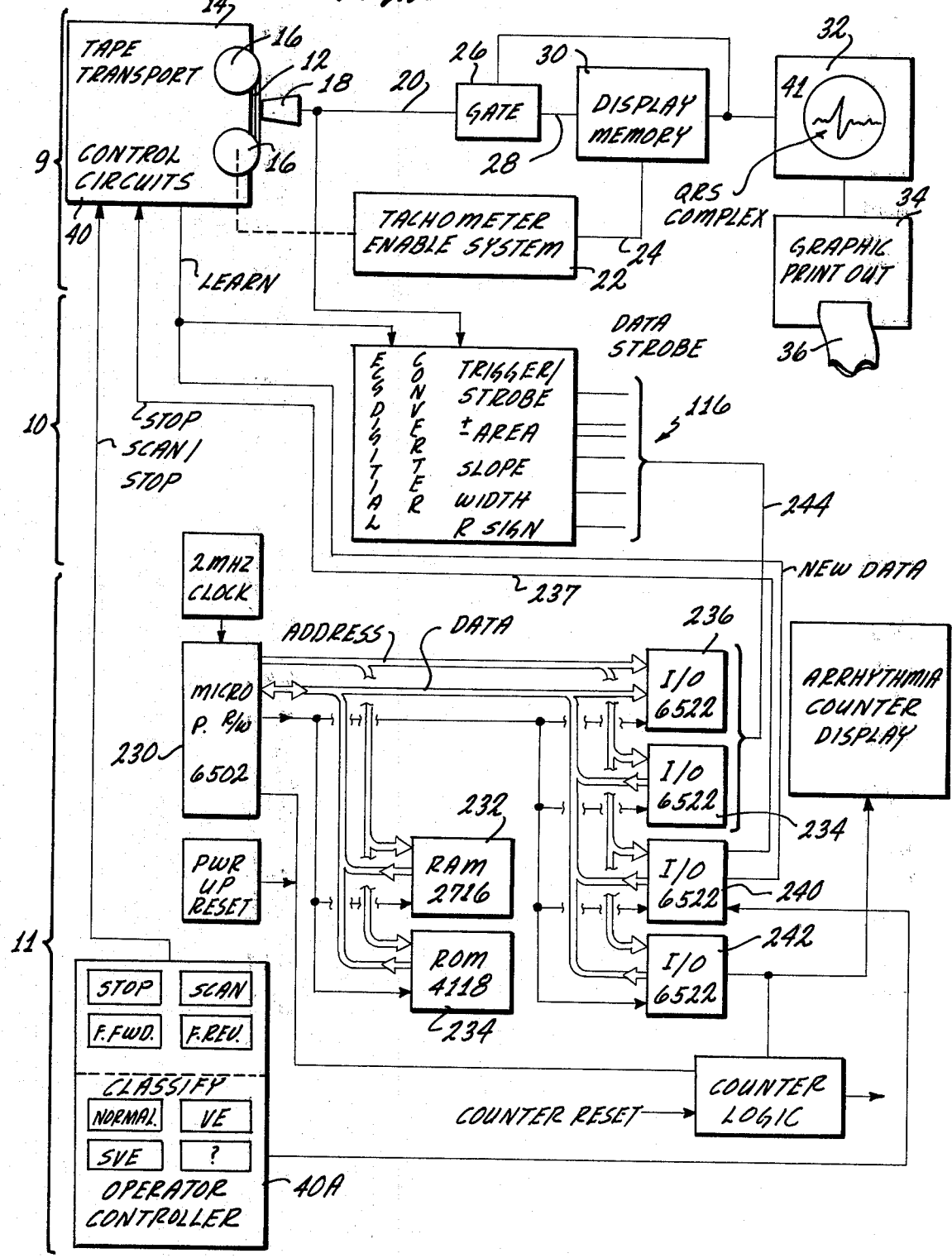

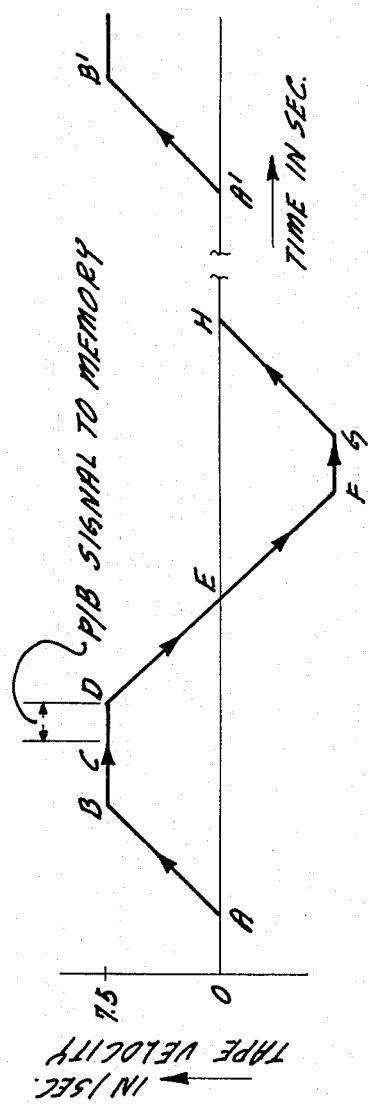
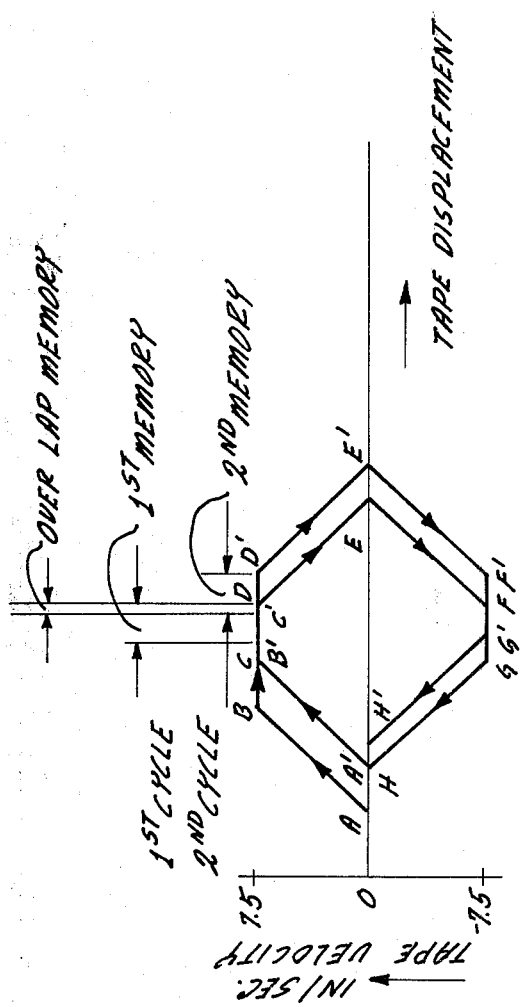

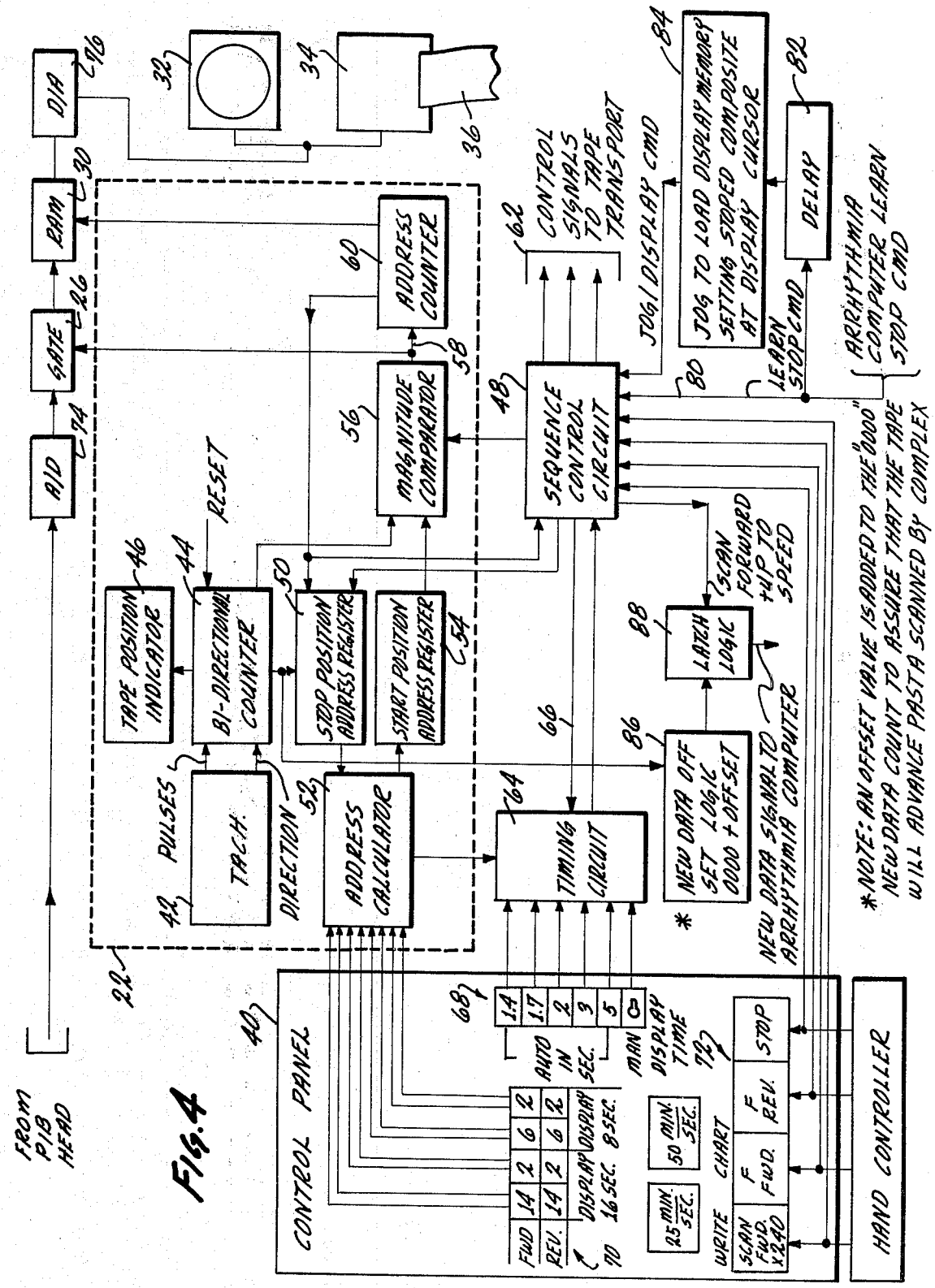

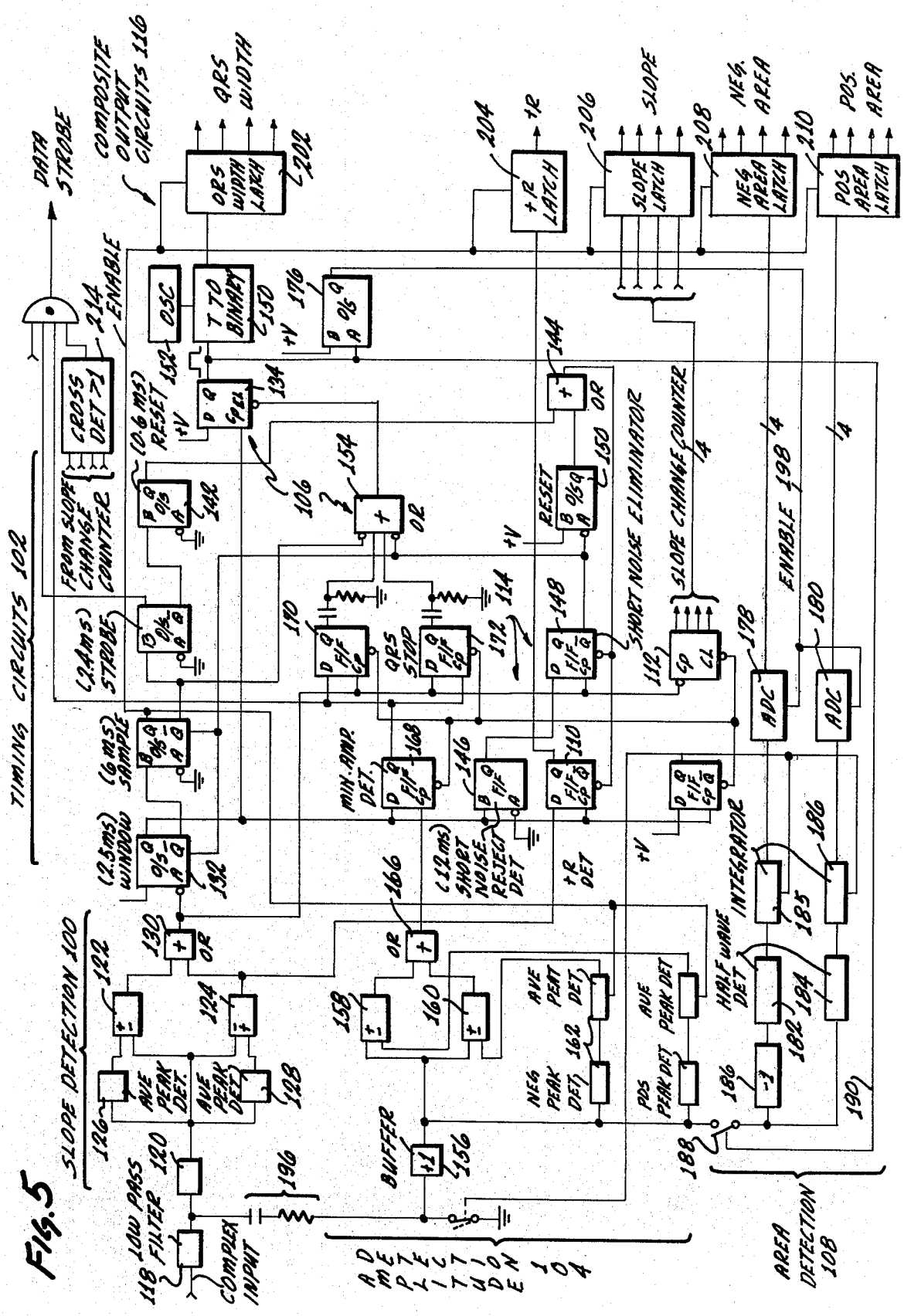

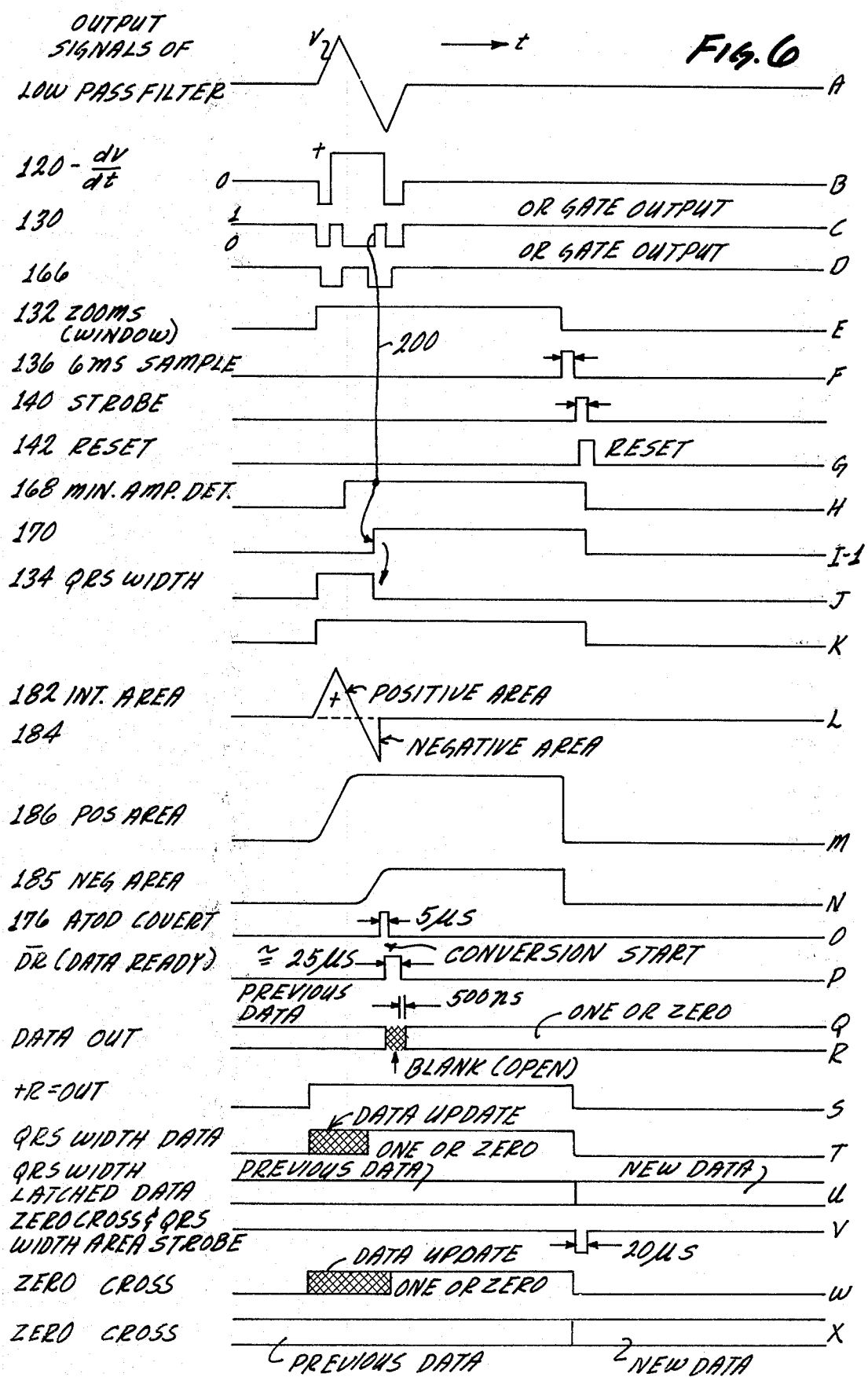

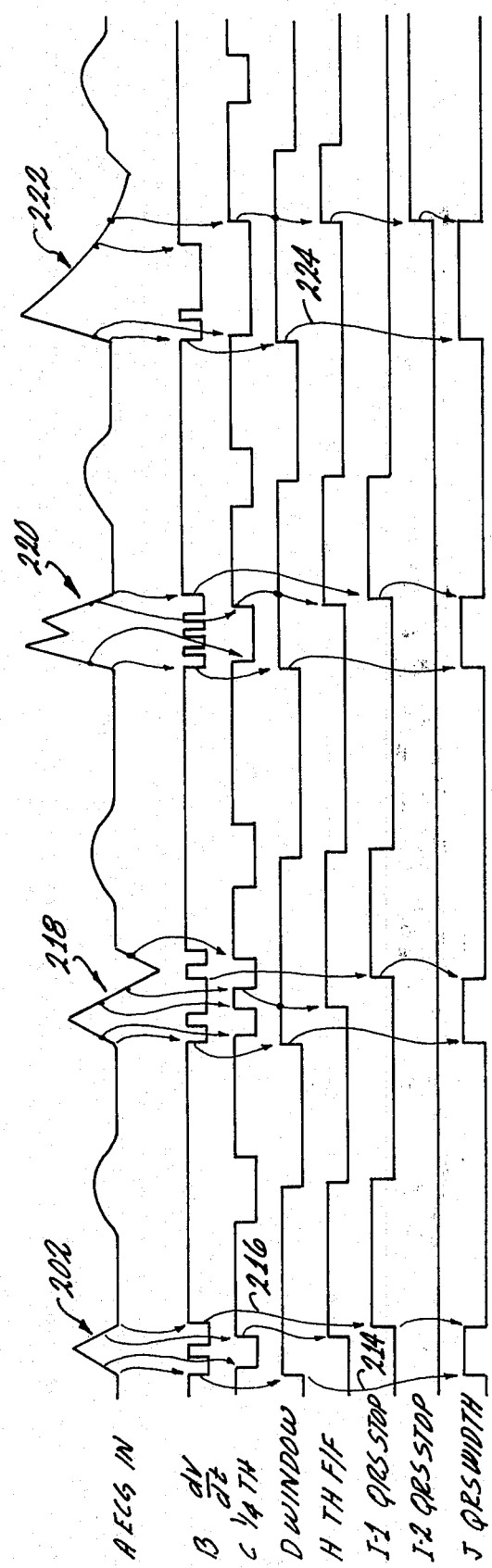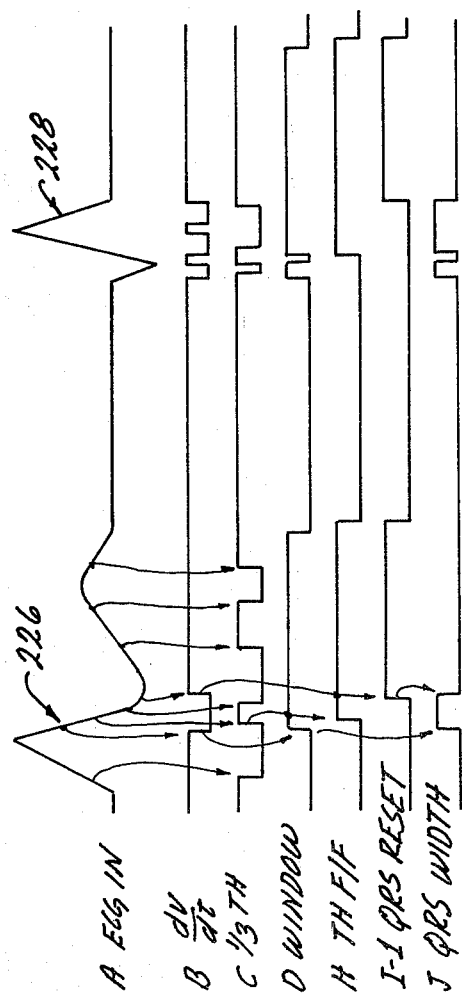
Fig. 7

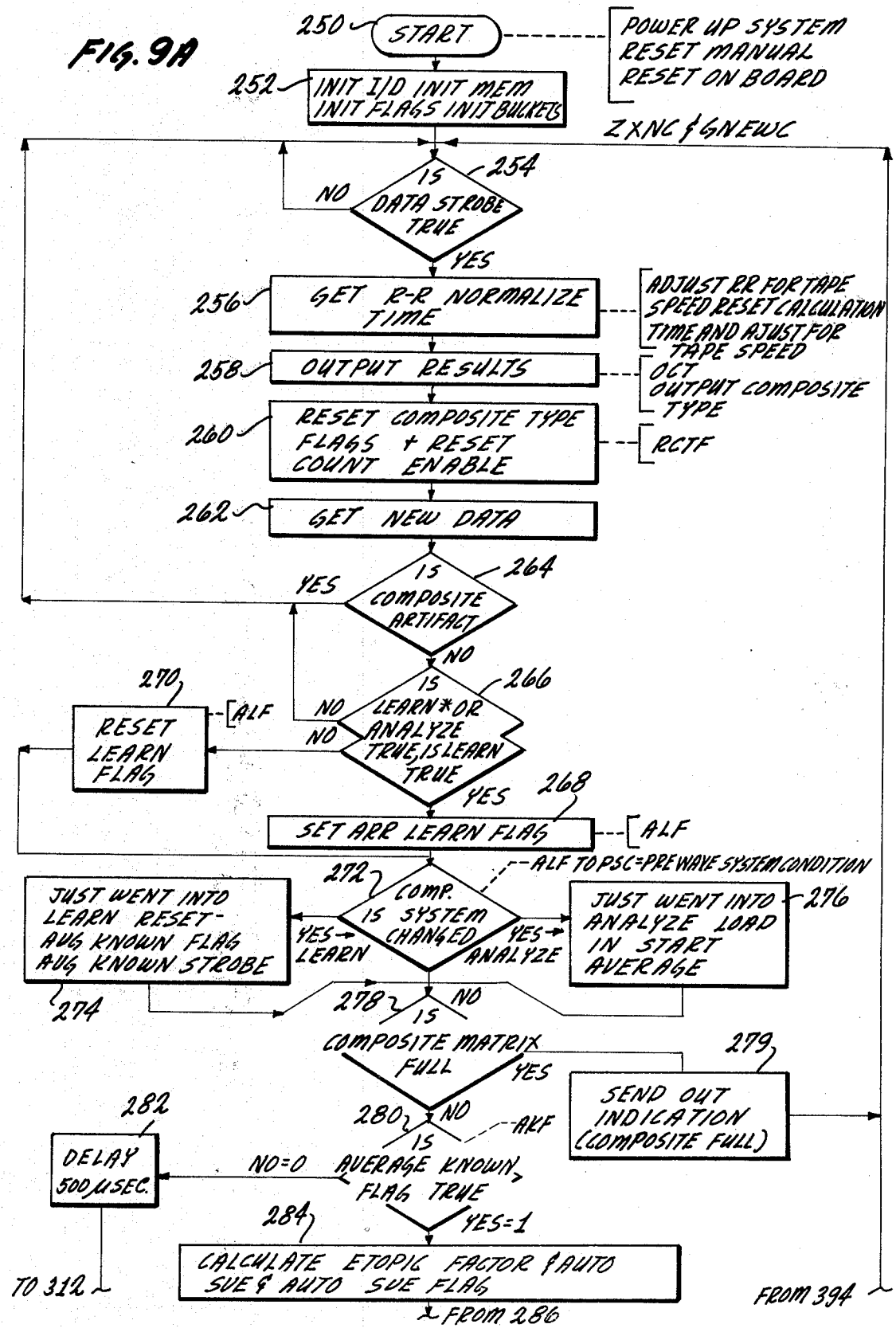

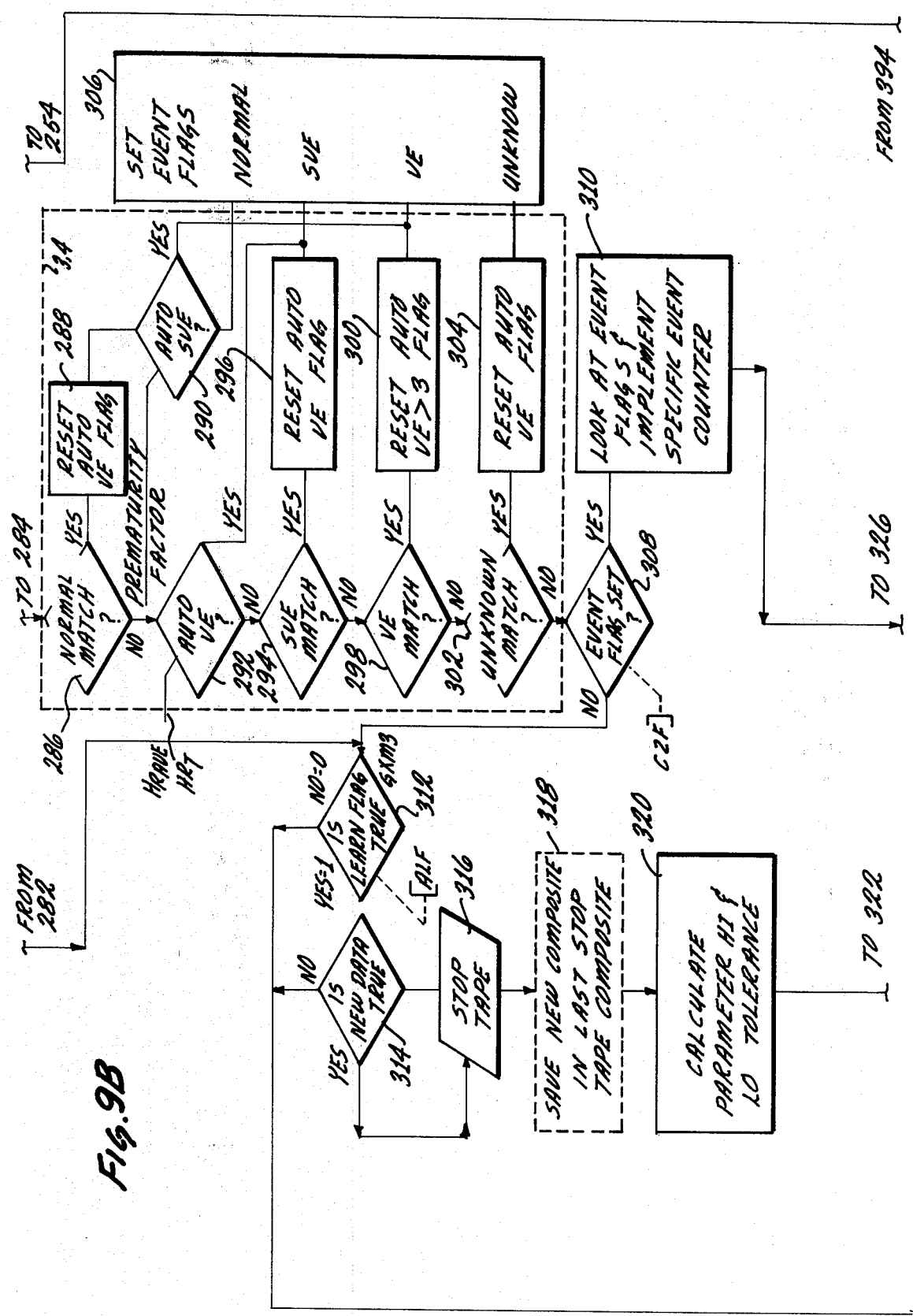

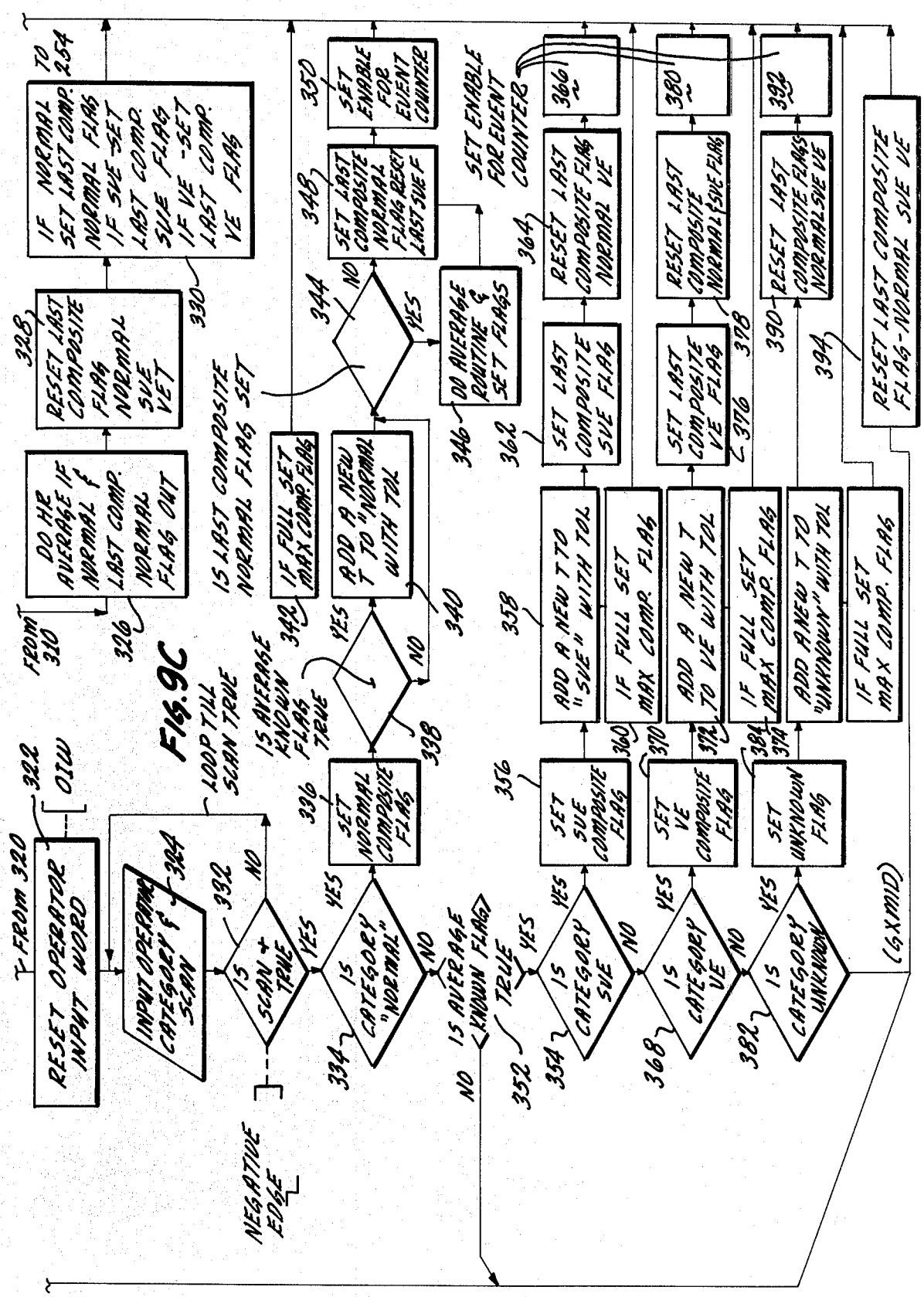

METHOD AND APPARATUS FOR ARRHYTHMIA ANALYSIS OF ECG RECORDINGS

BACKGROUND OF THE INVENTION

The present invention relates to electrocardiology and in particular to an arrhythmic analyzing system for electrocardiographs and more particularly to such a system for digitally scanning and characterizing arrhythmic electrocardial signals during high speed playback of ECG recordings.

Electrical signals that appear at the surface of a subject's skin as a result of the electrical activity within the heart are known as ECG signals. These ECG signals exhibit particular wave forms which correspond to the action within the heart muscle and reflect both in timing and in character the condition of the heart. It is well known to place electrodes on the patient's skin to sense the ECG signals and to present them for visual analysis either in real time or at a subsequent time for use by a physician or other trained personnel. Of interest to the physician is an analysis over an extended period of time of a continuous ECG signal which reflects heart activity during the normal activities of the patient and which displays anomalous heart signals which represent arrhythmic and ectopic activity. As used herein arrhythmic heart activity includes activity which is abnormal, such as irregular variations in rhythm and ectopic activity such as other arrhythmia, ventricular ectopic beats and abberently conducted supraventricular beats. More specifically, it is desired to accumulate and analyze large volumes of ECG signals during normal activities of the patient as for example over a twenty four hour period and to review this accumulation in a highly accelerated mode to determine the frequency and character of the various heart signals. For this purpose, there are known systems which accomplish the foregoing by recording the ECG signals in real time on a small, compact tape recorder which is worn by the patient. The recorded signals are then processed by replaying the same at a much faster speed with a presentation of the signals on a cathode ray oscilloscope in which each ECG complex is superimposed on predecessor complexes. This type of display is known as a Holter display, and a description of such a system is set forth in U.S. Pat. No. 3,215,136 issued Nov. 2, 1965 in the name of Norman J. Holter, et al. The scanning device of U.S. Pat. No. 3,215,136 utilizes superimposition of the ECG signals from two different tracks of the magnetic recording tape. A subsequent improvement is set forth in U.S. Pat. No. 3,718,772 issued Feb. 27, 1963 in the name of Clifford Sanctuary.

U.S. Pat. No. 4,157,571 issued June 5, 1979 to Steven K. Shu discloses an improved scanner in which the tape is reviewed by the Holter technique at high speed. The operator is also able to stop the high speed Holter display and to initiate a real-time single-frame viewing mode in which a segment of tape is repeated, any interval of the signal representing a frame stored in digital memory, and the content of memory displayed in real time for analysis by the operator and selected printout as desired.

Prior art scanners have also included provision for analyzing the signal to detect various abnormalities.

Normally the ECG signal results from electrical impulses that are generated to initiate the polarization of the ventricles of the heart at contraction and this signal is commonly referred to as a QRS complex. Immediately preceding this complex there is a small pulse that represents the initiation of the muscular activity and is referred to as a P-wave. Following the QRS complex there is at least one additional pulse commonly referred to as a T-wave. It is separated from the QRS wave by the so-called ST segment. Following the completion of each pumping action and prior to the succeeding pumping action, the heart relaxes and the ECG signal is essentially quiet with little or no fluctuation in electrical output.

In electrical pulses from a normal heart, the rhythm and the shape of the QRS complex are found to have certain predetermined characteristics which fall within certain limits. However, in the event the heart is subjected to abnormal strain or has infirmities, the ECG signal may exhibit more differences from a normal ECG signal. For example, the rate and rhythm of the heart beat may be erratic and may vary throughout wide limits. In addition the size, shape, and duration of the QRS complex and ST segment following that may substantially vary from the normal. These are generally termed ectopic beats, the most important being ventricular ectopic (VE) and supraventricular extopic (SVE). In general the cardiologist needs to know the number of VE and SVE beats in a given time interval.

U.S. Pat. No. 3,267,934 dated Aug. 23, 1966 to William E. Thornton entitled Electrocardiac Computer provides a means responsive to one or more of the characteristics of each QRS signal to measure its value and to detect the occurrence of ectopic beats, ST segment depression, pulse rate arrhythmia and other characteristics. U.S. Pat. No. 3,267,933 to W. E. Mills et al., dated Aug. 23, 1966, U.S. Pat. No. 3,858,034 to Donald L. Anderson dated Dec. 31, 1974, U.S. Pat. No. 4,006,737 to Isaac R. Cherry dated Feb. 8, 1977, and U.S. Pat. No. 4,073,011 to Isaac R. Cherry et al. dated Feb. 7, 1978 all disclose various computer-assisted analysis systems for processing cardiographic signals derived from high speed scanning of ECG tapes. These systems provide for identification of normal ventricular ectopic (VE), supraventricular ectopic (SVE), and other abnormalities and for accumulating a readout totalling such events over a scanning period. To do this, provision was made for establishing a set of signal threshold conditions against which each complex was compared, specifically with respect to pulse rate prematurity of the R—R intervals, R-wave, width, and R-wave amplitude. In general, such systems are either preset, i.e., contain a single set of built-in measures that determine excessive QRS width, amplitude, or other characteristics which are used to identify ectopic beats, or provide for operator analysis and selection from among a single set of predetermined characteristics for characterizing ectopic beats. It has been found, however, that it is difficult, if not impossible, to adequately establish a single set of predetermined criteria for normal, VE, and SVE beats which can be built into the analyzing circuitry of the scanner for satisfactory arrhythmic analysis, for it is desired to take into account the difference between patients in that normal VE and SVE beats vary widely from patient ot patient and can also vary with the particular ECG hookup or the position of the torso. Referring particularly to U.S. Pat. No. 4,076,011, the arrhythmia computer there provided for the automatic detection of an unusual event within the ECG signal such as the occurrence of ectopic beats. Provision was made for the operator to select whether or not to use present criteria for prematurity, width, amplitude and to select a single width value limiting normal events. The recommended procedure for selecting appropriate ectopic criteria called for the operator to scan a portion of the patient tape containing ectopic activity and to obtain a sample writeout. The writeout was then measured and used to determine which of the selectable criteria of the arrythmic computer were to be activated for counting ectopic occurrences on each individual patient tape recording. After the criteria were selected the entire patient tape was then rescanned to provide a complete analysis and digital display of totalled VE and SVE beats. While that system provided valuable assistance in the analysis of Holter-type recordings, it suffered from certain disadvantages and limitations, specifically the criteria for selection and classification of ectopic beats were built into the system and, once selected, became a single set of nonadjustable criteria. Additionally, whether or not each of the criteria should be employed required an operator choice and physical measurement of selected writeouts after reviewing the considerable portion of ectopic activity. Also, the variations in characteristics between abnormal beats exhibited within a given patient are often such that the criteria set for one abnormal beat will not permit another different beat to be detected. Thus, such prior art systems did not allow for adequate variation in selection of the various criteria by which VE and SVE activity were to be measured to accommodate patient differences and provided no breadth or range in the criteria used, once those criteria were selected. There is, therefore, a need for a new and improved ECG analysis system.

OBJECTS AND SUMMARY OF THE INVENTION

It is the general object of the present invention to provide a method and apparatus for arrhythmic analysis fo ECG recordings which will overcome the above limitations and disadvantages.

It is the further object of the invention to provide a method and apparatus of the above character in which an operator input is programmed to recognize each patient's unique ECG complexes and then to detect patterns of occurrence for clinically significant ventricular, supraventricular, and other arrhythmic occurrences.

It is a further object of the invention to provide a particular combination of analog and digital circuitry which is time-efficient in scanning tapes and processing in the resulting data at high tape speed playback (i.e., at ×240 or higher speeds) of prerecorded magnetic tape recordings of ambulatory patients. The method and apparatus employsed provides a machine time-efficient analysis wherein analog measurements are performed when it is most efficient so to do, and digital measurements and computer algorithms are performed when they prove to be the most efficient technique.

The method and apparatus of the present invention generally operates in two successive scan modes during each of which the entire patient tape recording is scanned. These modes are termed the learn mode and the analyze mode. In each mode and during scanning, each complex which occurs is detected and its wave shape is characterized into a digital pattern called herein a composite which thereafter represents the complex. Preferably, the digital pattern includes measurements of the plus and minus area of the pulse or complex, the number of slope changes, the QRS width in time and the initial R-wave sign of the complex. This digital pattern or composite is compared by suitable circuitry against known digital patterns previously recognized and stored in a digital memory. Such known patterns are termed templates and include tolerances for broadening the range of values they represent, as will be described. If there is a match between a new composite and an existing template stored in memory, the event, i.e., or complex, is then characterized accordingly.

The learn mode serves to identify the various types of complexes unique to the patient and to store them into the template memory for later use. Thus, during the learn mode, the tape is scanned at high speed to produce a Holter-type display and associated arrhythmiagraph. Each complex is converted into a digital composite as previously described and compared against known templates. Initially, the template memory is empty and, therefore, no match will be found. On no-match condition, in the learn mode, the present invention is designed to automatically stop scanning of the recording and to display the first complex in real time on an oscilloscope for classification by the operator. For this purpose, an operator input selector is provided by which the operator selects a given classification of the complex, a template is then formed and deposited into any of the several memory bins classified as normal, SVE, VE, or unknown. After classification the operator initiates continued scanning of the tape, during which each matched event is classified and counted in high-speed playback while each subsequent unrecognized complex causes the recording tape to be stopped and a display of the respective unmatched complexes to be given. As the tape is scanned and classified, the template memories are gradually filled and more matches are formed so that fewer and fewer incoming complexes stop the apparatus for operator classification.

It is found when utilizing the template classification in accordance with the present invention that the unique ECG complexes of each patient tend to cluster about data centers such that only a few templates of each category are needed to provide significant subsequent recognition. In some cases, as few as ten normal templates can characterize an entire recording. Similarly, it is found that multiple clusters of VE and SVE template serve to provide subsequent recognition and identification of a significantly large number of ectopic event occurrences based on relatively few stored templates. The invention also provides for the classification of certain events on the basis of changes or criteria derived from heart beat rhythm in combination with composite identification which are termed auto SVE and auto VE tachydardia.

After the entire tape has been scanned in the learn mode and the complexes on the tape have been classified and the templates formed and stored as set forth, the entire tape is rescanned in a second mode termed the analyze mode. During the analyze mode, all of the stored templates and conditions are searched in a pattern to determine whether any match can be found between an incoming digitally-characterized complex and a specific template or rhythm condition. The output results in a complete tape classification and can be read as normal, VE, SVE or unknown ectopy events rather than by the hour or for an entire recording. Various event memories and heart rate criteria can be provided and combined to give other rhythm morphology outputs in addition, if desired. The method and apparatus of the present invention provide an output event counter and a display which give a summary narrative or hourly tabulation for heart rate, ventricular and supraventricular ectopic activity.

These and other features and objects of the invention will become apparent from the following detailed description and claims when taken in conjunction with the accompanying drawings.

BRIEF DESCRIPTION OF THE DRAWINGS

FIG. 1 is a flow diagram outlining the general method for arrhythmic analysis of electrocardiograph recordings in accordance with the present invention;

FIG. 2 is a general block diagram of apparatus for analyzing electrocardiograph recordings in accordance with the method of FIG. 1 and constructed in accordance with the present invention;

FIG. 3A is a timing diagram showing the velocity of magnetic tape during analysis and one tape movement cycle in the operation of the apparatus of FIG. 2;

FIG. 3B is a diagram showing the relationship between tape velocity and tape displacement in the operation of the apparatus of FIG. 2;

FIG. 4 is a detailed block diagram of a frame-by-frame memory display system modified for use in the present invention;

FIG. 5 is a detailed block diagram of an ECG signal converter or composite generator of the apparatus of FIG. 2 and constructed in accordance with the present invention;

FIG. 6 is a series of graphs of wave forms and signal conditions generated within the circuitry of FIG. 5 in accordance with the present invention;

FIG. 7 is a series of graphs illustrating signal conditions within the circuit of FIG. 5 in response to QRS complexes of varying shape;

FIGS. 9A through 9C are detailed flow charts of the main software routine and logic for operation of the computer and comparator of FIG. 2 and as set forth in accordance with the present invention;

DESCRIPTION OF THE PREFERRED EMBODIMENT

Figure 8A:
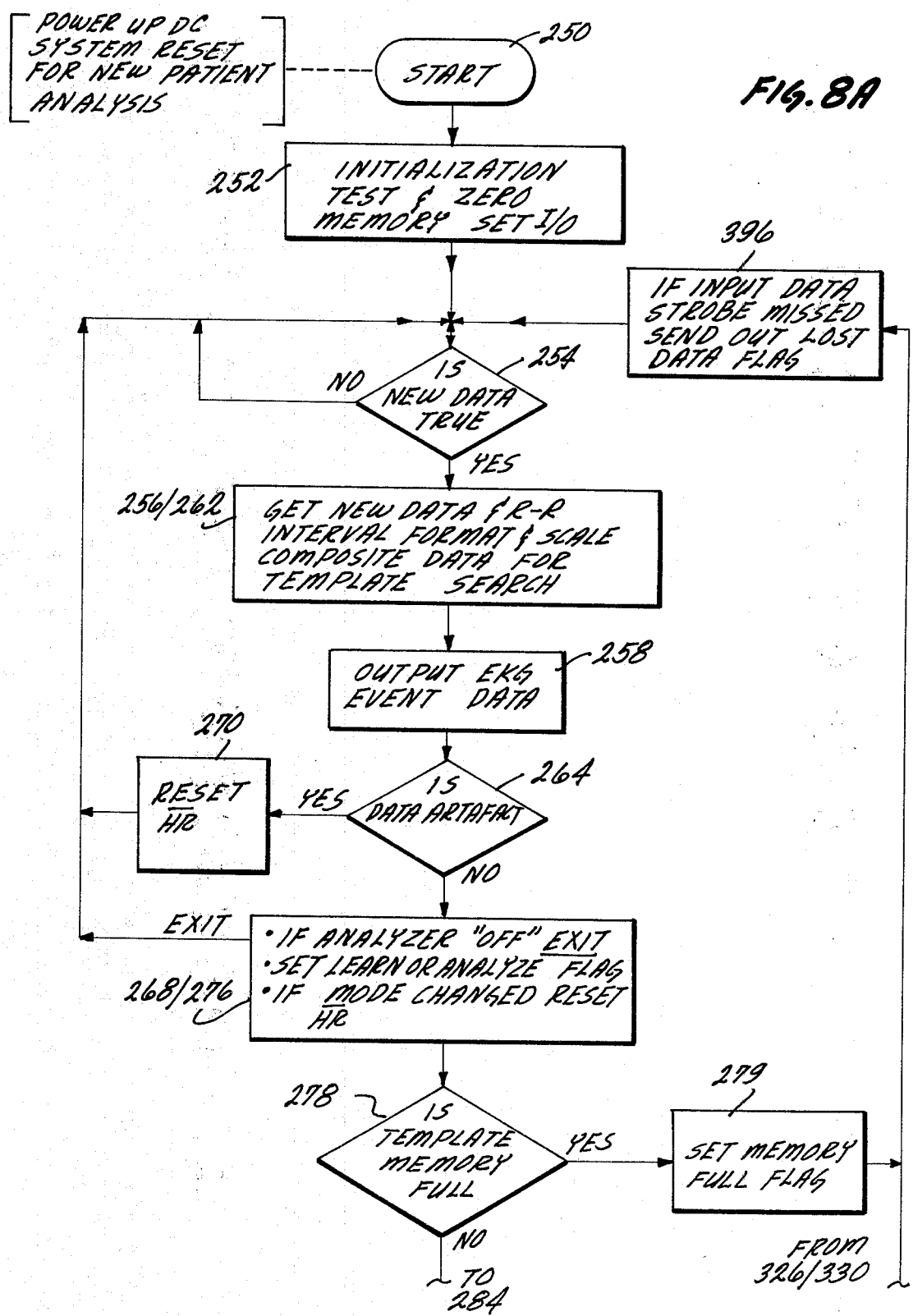
FIG. 8 is a simplified flow chart controlling the operation of the event computer and comparator of the apparatus of FIG. 2, in accordance with the invention.

Referring now to FIG. 1, there is shown a basic flow diagram in which the steps of the method of the present invention are outlined. Thus, in step 1, a tape recording containing an accumulated volume of ECG signals taken over an extended period is scanned at high speed on a tape playback scanner. Such recordings are generally known as Holter recordings and are accomplished by recording the ECG signals while a patient is engaged in normal activities on a small compact tape recorder which is worn by the patient. The recorded ECG signals are replayed at a much faster speed, as, for example, 60, 120 or 240 times the recording speed and displayed as a presentation on a cathode ray oscilloscope of the scanner. During the high speed scan, each successive ECG complex is superimposed on predecessor complexes to provide a superimposed stable image in fast time known as an AVSEP ® display. Such a scanning system and associated displays are disclosed in U.S. Pat. No. 3,215,136, issued Nov. 2, 1965 in the name of Norman J. Holter et al, which is incorporated herein by reference. Also incorporated herein by reference are U.S. Pat. No. 3,718,772 issued Feb. 27, 1973 in the name of Clifford Sanctuary and U.S. Pat. No. 4,006,737 issued Feb. 8, 1977 to Isaac R. Cherry which disclose methods and apparatus for a high-speed scanning of Holter tape recordings including systems for the production of trigger signals used to control the sweep of display oscilloscopes to produce a stable display and superimposition of successive ECG complexes.

The output of step 1 consists of a series of analog electrical signal pulses which correspond to the electrical eart activity of the patient. Each signal pulse is termed herein a complex and is generally referred to by electrocardiologists as the QRS complex. Immediately preceding each complex, the ECG signal contains a so-called P-wave and immediately following the complex there occurs a so-called T-wave. In the present invention, it is the analysis of the shape and successive timing of the QRS complex itself which is of primary interest. In step 2, the analog or video signal representing each individual complex is converted into a digital composite which is used as a representation of the complex for subsequent analysis. In accordance with the present invention, particular parameters of the complex are selected for conversion into a digital form which, when collectively taken together as a digital composite, serves to adequately characterize the shape of the respective QRS complex and to distinguish it from other complexes having significantly varying shape. It has been found that the following parameters are suitable and sufficient for such a characterization; namely, the QRS pulse width, the plus or minus area of the R and S waves above and below base line, respectively, the number of slope changes in the R-wave and the initial R-wave sign. The specific definitions of each of the above will be given in connection with the detailed description of the apparatus for carrying out the present method to be hereinafter described. It should be pointed out, however, that the shape of the R-wave of the QRS complex is generally arbitrary.

The classic normal QRS complex contains a positive going, fast rising initial R-wave which progresses into a negative going S-wave and terminates. In general, its positive area is defined as the integral of the R-wave strength with respect to base line from its onset to the beginning of the S-wave at the point where the signal first crosses the base line. Its QRS width is that time interval beginning with the onset of the R-wave signal to the nadir of the S-wave, i.e., the time of maximum S wave signal and the point at which the slope of the S-wave changes. The minus area is the integral of the signal QRS complex strength from the time where the R-wave crosses the base line and terminates to the nadir of the S-wave. The R-wave sign is either plus or minus as the initial R-wave is positive (R) or negative (S) with respect to base line. The number of slope changes refers to slope changes within the QRS complex and it is determined by the differentiation circuit and counter. The composite is given by this group of five digital numbers (width, R-sign, slope, plus area, minus area) which are digitally processed in accordance with the remaining steps of the present invention.

The digital composite of successive signals as produced in step 2 are inputted to a computer and compared in step 3 with known template patterns stored in a template memory divided into bins based upon classification of previously-identified complexes and designated as normal, ventricular ectopic, supraventricular ectopic, and unknown (ectopy of unkown origin). "Unknown" refers to arrhythmia event or complex which cannot be positively identified as VE and SVE, but nevertheless deserves independent consideration and identification as an arrhythmic event. In step 3 each incoming composite is compared, seriatim, with the templates stored in memory 4 or other predetermined condition to determine whether there is a match or no match between them. If there is a match the comparison results in an output signal indicating the event classification which is accumulated in a suitable arrhythmic event counter and display unit 5, and the scanning of the tape is continued. In the event that a no-match condition is found and the procedure is in the "learn" mode of operation, the procedure continues to step 6.

It will be noted steps 1, 2 and 3 together with utilization of template memory 4 and counter and display 5 are simultaneously operated during the learn mode of operation. Upon identification of a no-match condition, step 6 generates a stop command which ceases steps 1, 2 and 3 in progress and generates a short, time-lapse display of the unmatched complex from a display memory. The display is provided by substitution of the time-lapse single-frame display for the Holter display previously being given on the oscilloscope. The operator inspects the displayed complex and makes a classification in step 7 whether the unmatched complex is normal VE, SVE or unknown. This classification is added to the counter and the display unit 5. In step 8, a new template is made from the unmatched composite and this template is added to the template storage memory 4. Thereafter, in step 9, a scan command is generated which reverts the system back to the scan tape, step 1, for continuation of steps 1 through 3 until the next no-match condition is found. This procedure is repeated during the entire first learn scan of the tape during which the various template bins of template memory 4 accumulate respectively a plurality of composite patterns which have been classified and which represent a unique characterization of the ECG signal of the respective patient based upon a plurality of representative classified events for each classification. During the initial phase of the learn scan mode of operation, little data is available because there are initially no stored templates representing the patient's ECG complex classification. As scanning progresses, a build-up of known data is stored in the template memory and scanning proceeds at an increasingly faster pace since more known templates are available for characterizing incoming complexes and, thus, a higher percentage of matches will be found.

After completion of scanning of the entire tape, the tape is rewound and steps 1 through 3 are repeated in analyze mode. During this mode the tape is not stopped but is scanned from end to end and accumulated totals of event classification are made in display 5 and presented as total VE, SVE heart beats as well as total heart beats broken down in any desired manner as by time. The resultant data can be combined with heart rate data to provide various arrhythmia displays. The displays may include not only direct counts of arrhythmic events, but also other abnormalities which relate the events to each other and to the time of occurrences, such as ventricular bigeminy, coupled or paired beats R-on-T, tachycardia, pause, dropped beats, bradycardia, and others.

Heretofore, efforts have been made to analyze ECG signals by computerization. In general, the techniques previously employed have used complete digitization of the entire ECG complex, particularly, the R and S wave portions of the ECG complex. Some efforts have been made to analyze the complexes using parameter selection. However, the manner in which prior art efforts have developed require the utilization of a digital computer to process the analysis and characterization of the signal, as well as the ultimate characterization. When a requirement is set that tapes be scanned at 240 times actual recorded speed, a very time-efficient electronic realization is required in order to process the resulting data. This is because when maximum rate complexes are occurring, at for example, 180 beats/minute or 3 beats/second, a scan at 240 times real time requires a 750 complete ECG complex analysis or 200 to 500 times per second of real time, or actual recorded time. When this is played back, the analysis becomes extremely difficult and well-nigh virtually impossible to accomplish. This is because a 200 sample/second rate reaches computer speed limitations. This is seen when it is realized that at least 28,000 operations per second may be required for such an analysis, which, when coupled with the requirements of the associated digital program, leads to speed requirements for digital computers that are beyond that available today in the art of micro-computer technology. To get around this problem, the present invention proposes performing the primary ECG parameter characterization in analog circuitry as the data is being accumulated at a high rate of speed, then transferring the data for storage and computation, which requires no digital time or manipulation. A particular advantage as the rather considerable amount of manipulation time required to integrate the areas under the ECG curve is eliminated from the digital computer's computation. Thus, the computer portion of the data processing arrangements of the present invention may be restricted to very short time requirement manipulations and storage; and thereby permit and facilitate the analysis. More particularly, the digital computer portion of the present invention takes pre-digitized samples from the analog arrhythmia analyzing structure and forms them into a sequence which corresponds to the already analyzed data and then simply proceeds to do things which the computer can accomplish simply and efficiently; i.e. searching the various templates to compare a match or no-match condition. In addition, the digital computer portion of the invention can be employed to do other non time consuming tasks, such as determining automatically SVE criteria and generating the necessary signals for related counters for tape deck and learn stop signals.

In addition, upon reply on apparatus of the present invention, each complex on the recording is identified by a time index code (established by a tachometer circuit to be described), so that a suitable memory can be provided for memorizing and recalling each abnormal event by type of classification and time index for real time printout, if desired.

Referring now to FIG. 2, there is shown a simplified block diagram of apparatus for carrying out the method of the present invention, and it consists of three main sections, a recording scan and complex display section 9, a signal converter section 10 for generating a digital composite, and carrying out the step 2 of the method, and a computer and comparator section 11 including template memory 4 for carrying out steps 3 through 8 of the method.

The scanning section 9 of the present invention as disclosed in FIGS. 2 through 4 hereof are adapted from the system set forth in U.S. Pat. No. 4,157,571 dated June 6, 1979 to Steven K. CHu, and assigned to the assignee of the present invention. As much of the referenced patent as is pertinent hereto is repeated in order to complete this disclosure, together with such additions and modifications thereto to show how the same is utilized herein. Thus, it is assumed that ECG signals have been previously recorded on a suitable magnetic tape 12 in the manner of the Holter technique. The tape 12 is inserted into a tape transport 14 for playback. The tape transport includes the reel 16 and a drive system turning them under control of an operator selectively in either forward or reverse directions. The playback (P/B) head 18 converts to signals stored on the magnetic tape into an electrical analog signal on conductor 20. As set forth, it is necessary to determine which point on the magnetic tape is producing the signal on conductor 20 and the complex and composite generated at any particular time so that when a no-match condition is found, it will be possible to carry out the step 6 of stopping and displaying the respective complex for classification by the operator. Thus, the system will be able to locate the exact same point in time on the tape for display on command. It is imperative that this point be precisely located so that the operator can be sure exactly what portion of the complex tripped the stop command. To accomplish this, a tachometer system 22 is associated with the tape transport 14 to generate an indexing system for the tape 12. The tachometer includes an optical pickoff which generates electrical pulses as the tape 12 moves over a capstan (not shown). These successive electrical pulses are then counted to provide an accumulated total count which can be used as an index of position along the tape. In order to display the portion of the tape 12 following a predetermined point on it, the index number corresponding to the predetermined point is compared to a continually-increasing index number generated by the tachometer system as the tape moves, and, when the two numbers are equal, the predetermined point has been reached. At that time the tachometer system generates an enabling signal on conductor 24 to enable a gate 26 to pass the playback signal on conductor 20. The gated signal is then applied on conductor 28 to a display memory or storage device 30 for later display. The storage device is capable of accepting the serial signal on conductor 28. Normally, suitable analog-to-digital convertors will be required if a digital memory 30 is employed.

The signal stored in memory 30 consists of an appropriate time interval of the output of the tape 12 and may be replayed on a display unit 32, such as an oscilloscope display. Upon operator command, the stored signal can be additionally applied to a graphic recorder to produce a permanent record 36 in chart or printed form.

Although the representation produced on the display 32 and the record produced by the recorder 34 are continuous in time, the playing back of the magnetic tape 12 is intermittent. A selected segment of the magnetic tape 12 is played at high speed and the signal produced is stored in the storage device 30. Because the segment of tape is played at a speed greater than real time, the information is stored in the storage device 30 before it is needed by the display 32 to produce a real-time display. Therefore, some of the information remains in storage until the time when it would have occurred at real time.

Because the magnetic tape 12 is played back intermittently at high speed, consideration must be given to the time and distance required for the tape to accelerate to and decelerate from the high speed at which it is played back. Thus, the inertia of the tape drive system must be taken into account. Accordingly, in each tape movement cycle, the tape must begin its acceleration at a time and distance well in advance of the segment of the tape chosen for playback. This is illustrated in FIGS. 3A and 3B which describe the motion of the magnetic tape during a complete tape movement cycle. Normally, the length of the segment of the magnetic tape is an integer multiple of the duration of the signal representation displayed on the display unit 32. That is, the segment equals one or more frames of the display.

In FIG. 3A the velocity of the tape in inches per second is shown as a function of time for the preferred embodiment of the present invention. If the interval CD represents the time during which the selected segment is played back, then the interval AB represents the time during which the selected segment is played back, and the interval AB represents the time (0.1875 seconds) during which the tape is accelerated at 40 inches per second squared. Assume the playing back is always done at 7.5 inches per second tape velocity and always in the forward direction of motion of tape. After the selected segment has been played back, the magnetic tape is decelerated during the interval DE, reaching zero velocity instantaneously at the time E. The deceleration continues during the interval EF resulting in a negative velocity, i.e., the tape moving in a reverse direction. During the interval FG, the tape is moved in reverse at a speed of 7.5 inches per second, and this movement is maintained for approximately 0.35 seconds. Finally, the tape accelerates during the interval GH to a stop at the time H. The tape then remains at rest until the next tape movement cycle begins at the time A.

In contrast to FIG. 3A, the graph of FIG. 3B shows the relation between the tape displacement and the tape velocity and relates to the same tape movement cycle as FIG. 3A, but describes it in a different manner. Thus, the acceleration phase is represented by the segment AB. After the tape has reached a velocity of 7.5 inches per second, it continues to move at that speed during the interval BD, during which the segment CD is played back. The tape continues to move through the interval DE as it decelerates to a stop. Thereafter, the tape is in the reverse direction as indicated by the points E, F, G and H. The point H coincides with the point A which is the starting position for the next tape movement cycle. In the next tape movement cycle, the segment is played back.

FIG. 3B shows a second tape movement cycle denoted by the letters A–H. The segment CD is seen to be displayed along the tape a short distance with respect to the segment CD of the first tape movement cycle. Also, there is an overlap CD between the played back segments CD and CD.

In connection with the description of FIG. 3A, the duration of time in which the tape was moved through the interval BD was not specified. That interval is determined by the operator of the apparatus and depends on whether the operator chooses to view successive segments progressing in the forward or in the reverse direction along the tape. The operator expresses his choice through a control panel 40 or associated hand controller 40A (shown in FIG. 4) through which he determines the length of the segment BD by actuating certain switches located on the control panel. In learn mode, the complex which was unmatched is jogged into the center of the display and into alignment with an indexing cursor 41 which will be more fully described hereinafter.

Turning now to block diagram of the scan section 9 as shown in FIG. 4, it can be seen that the tachometer system 22 includes a number of sub-systems which implement the movement of the magnetic tape as described in connection with FIGS. 3A and 3B. The tachometer 42 is an optical pickoff attached to a capstan (not shown) used for driving the tape and has a constant diameter and, hence, each pulse produced by the tachometer 42 represents the same distance along the tape and accordingly the same time interval. The tachometer 42 also senses the direction of movement of the tape. Pulses from the tachometer 42 are applied to the bi-directional counter 44, which accumulates them. The total number of pulses accumulated is a measure of the amount of tape which has passed over the capstan, and thus can be used as an index to the tape. The count on the counter is applied to the tape position indicator 46 to give a visual indication to the operator of which portion of the tape is being played. Upon issuance of a stop command by the operator through the control panel 40, the sequence control circuit 48 generates a series of commands to cycle the tape from the position D of FIG. 3A to the end of the tape movement cycle at point H, and the tape position indicated by the bi-directional counter 44 is stored in the stop position address rejector 50. When a command to advance to the next segment is generated by the operator through the control panel 40, the address calculator 52 reads the tape position stored in the stop position register 50, decrements it, and stores the result in the start position address register 54. The tape transport is then commanded to accelerate in the forward direction. After the magnetic tape has reached a speed of 7.5 inches per second and when the approximate tape position is reached to reload the memory 30, the sequence control circuit 48 activates the magnitude comparator 56 which continually compares the tape position as indicated by the bi-directional counter 44 with the desired starting address which is stored in the start position address 54. When the magnitude comparator 56 senses that the addresses are matched, it generates a signal on the conductor 58 which is applied to the gate 26 to permit the played-back signals to be gated into the memory 30. When the address counter 60 has sensed that the memory has been completely reloaded, it causes the sequence control circuit 48 to generate a series of control signals on the conductors 62 to cycle the tape transport from the D to H position and to store in the stop position address register 50 the reading of the bi-directional counter 44 corresponding to the position D.

When the position H is reached, the sequence control circuit 48 sends a signal to the timing circuit 64 via conductor 66 to indicate the end of the tape movement cycle.

The tape movement cycle can be repeated in a number of seconds selected by the operator by means of a series 68 of switches on the control panel 40. Preferably, one of the switches 68 produces an infinite time delay between cycles so that manual control is required in place of the automatic cycling feature during normal operation.

The control panel further includes switches 70 by which the operator can select, within limits, the length of the segment played back and the direction along the tape in which successive segments progress. Another series of switches 72 on the control panel permit the operator to move the tape rapidly in the forward and reverse directions and to stop the tape. One of the switches 72 permits the tape to be advanced at a speed suitable for scanning the tape initially to determine which portions of it are of interest. In the preferred embodiment, 11 seconds of data can be stored in the memory for presentation on the display 32.

Because the signal from the playback head is an analog signal, the analog-to-digital converter 74 is provided to convert the signal to digital form for storage in the random access memory 30. The signal recalled from the memory 30 is converted to analog form for display by the digital-to-analog converter 76.

Thus, when the learn stop command is received from section 11 and upon identification of a no-match condition, it is applied to the sequence control circuit 48 through line 80 which causes the system to recycle and to load the memory 30 with the data from the previous 11 seconds of ECG data. While this is taking place, a delay 82 is employed to permit sufficient time to lapse to permit movement and display of the stored data. The complex of interest is centered for examination by the operator by a jog circuit 84 which is employed to generate the jog display command so that the tape is cycled and advanced so as to present the next successive segment, i.e. segment to C' D' for viewing on the display. This circuit is adjusted to bring the exact complex causing these type commands into view and into alignment with the cursor 41. After identification and classification of the displayed complex, the operator enters a scan command in order to prevent reconsideration of the same complex by the subsequent data networks. An offset logic circuit 86 is connected to the output bi-directional counter 44 and offsets the count by an amount adequate to assure passage of the complex played complex during scan before a new data signal is generated. A logic latch 88 receives pulses from the sequence control circuit indicating the initiation of scan command, forward movement of tape and up-to-speed and combines it with a logic signal from circuit 86 indicating passage of the data count signal and offset to initiate a new data signal to be supplied to the computer and comparator of section 11.

Referring now to FIG. 5, the analog-to-digital composite generator or convertor section 10 of the present invention is shown in detail. The following definitions and explanations are given as useful in understanding the following description in relation to the ECG signal convertor for generating multiple word digital data composites corresponding to incoming analog signal complexes:

V is the analog ECG signal;
complex refers to so much of the ECG signal as normally includes the P-wave, the QRS wave, and the T-wave.
QRS or QRS complex is so much of the V signal exclusive of the P and T-waves. Q or Q-wave refers to the dip intiating the QRS complex. R or R-wave is the dominant portion of the QRS wave and in normal heartbeats is identified as a large, positive, fast-rise time pulse, from about 40-80 milliseconds duration. S or S-wave is the usually small negative wave which terminates the R wave of the QRS complex;

dv/dt is the differential of the analog ECG signal selected for processing and evaluation, and is referred to herein as the slope;

QRS width is that time interval from the onset of the QRS complex as measured from the time the slope of the complex exceeds a predetermined threshold value until both the amplitude and slope have fallen below predetermined threshold values;

slope also refers to change as that number of times the slope values exceeds a predetermined value within the QRS width interval;

R-sign is that sign of the value of the R-wave which first follows the initiation of the QRS width signal;

A+ area is the integral of the strength of the positive values of the first positive pulse of the QRS signal against time, and is taken from the initiation of the QRS width signal to either the (1) termination of the positive signal or (2) the end of the QRS width, whichever occurs first;

A− area is the integral of the strength of the negative values of the first negative pulse of the QRS signal and is taken from the initiation of the QRS width signal to either the termination of the negative signals or (2) to the end of the QRS width signal, whichever occurs first;

with respect to the positive or negative area as used herein, it will be noted that only so much of the actual positive or negative area of the second occurring pulse within the QRS pulse envelope is measured from the positive to negative transition (or negative to positive transition, respectively) to the nadir of the S-wave. This will be about ½ of the actual value but is proportional thereto and accordingly, useful;

composite or QRS composite is that group of digital data words selected to represent the measured parameters of the QRS complex and which serve to characterize the complex and thus form the basis of template memory. In the present invention, the composite includes the digital data words for QRS width, A+, A−, R-sign and slope changes;

template is a group of digital data words stored in template memory bins classified as normal, VE, SVE or unknown ectopy, and includes the data words of classified composites plus tolerances.

Referring specifically to the circuitry of FIG. 5, the specific logic hardware utilized to generate a composite is shown in detail. The circuits include a slope detection section 100, the output of which is a series of pulses which sets off the series of timing circuits 102, which places the remainder of the system in operation and starts the QRS width measurement. Amplitude detection circuits 104 in part control the measurement of QRS width circuits 106. Area detection circuits 108 measure the product of the strength of QRS signal as a function of time. R-sign detector 110 is is provided as well as a counter 112 for accumulating a total number of slope changes occurring during the complex measurement. A short noise circuit 114 resets the system whenever the input signal duration is less than that considered significant. The various circuits will now be described in detail.

Thus, there is provided means for measuring the slope changes and for developing a series of pulses whenever the slope change exceeds a predetermined value. Such means includes the slope level detector circuit 100 which takes the form of a differentiating circuit which receives the signal output from a low-pass filter which serves to eliminate high frequency artifacts. The output of circuit 110, −dv/dt, is taken in parallel to one of the inputs of a pair of threshold detectors 122 and 124, the other input to which is passed through signal average peak detectors 126 and 128, respectively, which are adjusted to maintain an average value of about the last 8 beats of cardiac activity. The output of the threshold detectors 122, 124 are "ored" in a logic circuit 130 to provide a combined pulse output whenever either output is present indicating the existence of a signal having a slope greater than the slope, either positive or negative, which is greater than one-third the predetermined values set by the average peak detectors 126, 128. The pulse output from circuit 130 drives a series of trigger circuits which are connected to operate in sequence, one following the other. The time values shown in the drawing are patient times, as distinguished from real-time operating speeds. Thus, the first, termed a window trigger, 132, is a monostable multivibrator having a duration cycle of 250 milliseconds, the Q output of which clocks QRS flip-flop 134 into an on state and also is connected to other circuit flip-flops to initiate the measuring cycle of the QRS pulse, as will be described. At the termination of the 250 millisecond duration of trigger 132, its $\overline{Q}$ output drives a 6 millisecond, one shot multivibrator 136 to generate a data sampling pulse at its Q output, the $\overline{Q}$ output driving a 2.4 millisecond strobe one shot multivibrator 140 to indicate a data ready condition. The latter's output termination signal at 140 $\overline{Q}$ drives a final one shot multivibrator 142 which serves to provide a system reset pulse at the end of the QRS measurement cycle. This pulse is supplied to another, OR circuit 144, the output of which is connected to the reset input of the various system components to be described. The other input of OR circuit 144 receives the output of short noise circuit 114. Thus, a one-shot multivibrator 146 has its high input connected to the output of window trigger 132 and initiates a high output of 12 milliseconds duration, which drives the D input of the flip-flop 148, the clock input of which is connected to the circuit 130. Whenever a slope change occurs within the 12 millisecond interval set by one shot 146, the flip-flop 148 is triggered and provides a $\overline{Q}$ output of which is connected to or circuit 144, as previously indicated. In this way, incoming pulses of less than 12 milliseconds duration are eliminated from detection or measurement.

Means is provided for detecting the initial R wave sign and consists of a D flip-flop 110, the D input of which is connected to minus threshold slope detector 124. The clock input of flip-flop 110 is connected to the Q output of window flip-flop 132. Thus, whenever the value of the slope is greater than the threshold value, the sign of the slope as set on the D input is transferred to the Q output of flip-flop 110. Accordingly, a positive slope will be indicated as a positive pulse at the Q output, and a negative slope will be indicated by a negative Q output.

Means is provided for measuring the number of slope changes of the input signal V and consists of a slope change counter 112 as for example a four-level shift register clocked by the output of the slope change OR circuit 130. Its output is a data word representing the number of slope changes and is given on data line 113.

Means is provided for measuring the width of the QRS signal and consists of a D flip-flop 134, the input of which is clocked on by the Q output of the window flip-flop 132 indicating the existence of signal having a slope value which exceeds the predetermined level. The Q output of flip-flop 134 controls a time-to-binary counter 150 which counts signals received from an oscillator 152. A QRS width stop circuit terminates in an output OR logic circuit 154 which is activated whenever any of its four inputs are present. One input is from the short noise eliminator 148 previously discussed. Another input is from the trigger sample circuit $\overline{Q}$ output previously discussed and indicating termination of both the window and sample intervals. In normal operation neither of these inputs will occur before the principal condition is established as hereinafter explained.

The QRS stop circuit generally provides means responsive to either of the following sets of conditions for supplying an output signal to the QRS stop OR circuit 154: first, the slope falls below the threshold value followed by the absolute value of V becoming less than threshold; secondly, the absolute value of V becoming less than threshold followed by the slope falling below threshold. In order to measure the absolute value of the input signal V, the amplitude detection circuits 104 are employed. Thus, the output of the low-pass filter is also applied through a buffer amplifier 156 to the input of parallel connected positive and negative threshold detector circuits 158 and 160, the other inputs of which are taken from respective series connected negative peak detector and averaging circuit 162 and positive peak detector and averaging circuit 164. The positive and negative peak detector circuits are enabled by the Q output of a sample circuit 136 during the close of the preceding complex measurement which is taken as a reference. Average peak detecting circuits are adjusted to maintain an average over a significant interval of QRS complexes typically about 4 to 20 in number to provide adequate sampling. Whenever the amplitude exceeds ¼ of the average amplitude as determined by comparators 158 and 160 an output pulse will be signalled by OR circuit 166 which clocks a minimum amplitude detector flip-flop 168, the D input of which is established by the Q output of flip-flop 132. Since the pulse from the circuit 166 follows the input from trigger 132, the minimum amplitude detector 168 Q output is activated only upon the condition that both amplitude and slope had exceeded the predetermined threshold values. The output of flip-flop 168 is taken to the D input of a QRS stop flip-flop 170 and to the clock input of a second QRS stop flip-flop 172. Now, if the slope changes, as evidenced by the output from OR circuit 130 at the clock input of QRS stop flip-flop 170, this can be understood to occur at the nadir of the QRS pulse, S wave. On the other hand, if the slope falls below a threshold value first, the D input flip-flop 172 will be activated and subsequently clocked by the minimum amplitude detector flip-flop 168 output. Conditions under which this occurs for particular input signals will be further explained in connection with the graph of FIG. 7. In either event, an output signal pulse is delivered to OR circuit 154 which resets flip-flop 134 and terminates the OR width pulse. The trailing edge of the QRS width pulse terminates the interval of counting as set by binary counter 150 so that its output is a digital word representative of QRS width. The trailing edge of the pulse also triggers a one-shot data conversion start multivibrator 176, the Q output of which enables analog-to-digital convertors 178 and 180 in area detection circuits 108 to be described.

Means are provided for measuring the positive and negative area of the input analog signal during the period of the QRS width pulse and consists of a pair of parallel-connected half-wave detectors 182, 183 the input to one of which is inverted by a minus 1 amplifier 184. The input to each of the area detectors is controlled by a switch 180 which is normally open and is closed during the presence of the QRS width pulse on line 190. The outputs of the half-wave detectors 182, 183 are integrated by circuits 185, 186 which are enabled by the output of flip-flop 187, which also serves to open normally closed switch 189 at the input of buffer 156. Flip-flop 187 is clocked on by the Q output of window trigger 132 and is reset by reset OR circuit 144. The switch 189 and associated RC network 196 serves to ground the base line of the incoming signal so as to present a stabilized input and to an arbitrary zero reference level during the QRS signal measurements taken by the circuits of FIG. 5. As indicated the output of integrators 184, 186 are converted into digital output by analog-to-digital convertors 178, 180 which are enabled at the close of the QRS signal for a predetermined period set by one shot 176 on line 198.

FIG. 6 is a series of wave forms A through X which indicate the interrelationship in time between the signals appearing at the outputs of various flip-flops and at various locations throughout the circuits of FIG. 5. It should be noted that the input signal was taken to be of the form having a significant positive R-wave portion followed by a significant S-wave portion. The arrow at 200 indicates the sequential logic involved in selecting the nadir of the S wave portion for termination of QRS width and negative area measurement. It should be noted that the occurrence of a slope change at the output of circuit 130 which has been preceded by the rise in the minimum amplitude detector output 168 causes flip-flop 170 to be clocked and also causes termination of QRS width signal 134. It can be shown that the symmetry of flip-flop 170 and 172 will cause similar timing diagrams in case the QRS wave is polarity-reversed. The remaining graphs in FIG. 6 are believed to be self-explanatory so that no further discussion is believed required.

Referring again to FIG. 5 the composite output consists of specific binary digit latch circuits as follows: first, a QRS latch 202 which receives the output of binary convertor 150; second, R-sign latch 204 which receives the output of R sign detector 110; third, a slope latch 206 which receives the output of slope change counter 112; fourth, a negative area latch 208 which receives the output of convertor 178; and lastly, a positive area latch 210 which receives the output of digital convertor 180. All of the latches are enabled by the Q output of sample one-shot 136 so the data previously held is replaced by current data available from the various circuits. This data is characterized as a specific digital word for each of the selected characteristics of the input signal which is measured. Together these signals make up a composite in digital form representing the character of the input QRS complex.

Means is provided for giving a strobe output signal at the termination of the sample interval and consists of strobe one-shot 140 which is triggered on by the closing output signal $\overline{Q}$ of a sample one shot 136. Further, the output strobe signal is inputted to a 4 input AND gate 211 which also requires a data valid signal to be present as well as a slope change measurement greater than one as indicated by a slope crossing counter 213. The fourth input is taken from the output of flip-flop 168 indicating that a pulse of magnitude greater than a predetermined threshold level has been received. When these are present, a data strobe pulse is outputted from gate 211 to signal the following data-processing circuit that a complete data composite output group is available from the latches 202 through 210.

FIG. 7 illustrates the wave forms of certain of the portions of the circuits of the FIG. 5 in response to QRS signals of varying shape. The signals are given letter designations A, B, etc. which correspond to the signals of FIG. 6. The first group generally designated by reference numeral 212 follows from a generally triangular QRS pulse as shown. The arrows interconnected between the various wave forms show the sequential logic of the wave forms in relation to each other. Thus, arrow 214 indicates that the QRS width window and the timing circuit window wave forms each follow from the initial condition that the slope signal exceed threshold value. The arrow 216 indicates that the QRS width is terminated upon the sequence that the amplitude has fallen below a certain value followed by a change in slope. This permits detection of the nadir of the S-wave which occurs at approximately base line. Wave 218 is representative of a typical Normal pulse in which there is both a significant R-wave followed by a significant negative pulse S-wave. As the arrows indicate, the QRS width is initiated by the slope change appearing on the signal 218B. The QRS width termination occurs when the slope changes at the S-wave nadir following the change in amplitude to a value less than threshold.

Wave 220 shows the result of an intermediate spike in the R-wave and indicates that the measurement of the total wave is not affected, since the spike does not drop to a level below amplitude threshold.

Wave 222 shows a condition in which the slope of the falling R wave falls below predetermined threshold value before the amplitude giving rise to the operation of flip-flop 172 and a QRS stop output pulse labelled 12 generally indicated by the arrow at 224.

QRS pulse 226 is illustrative of circuit operation when the QRS pulse has a slow initial rise time, and accordingly, has a slope insufficient to cause triggering of the various circuits. In that instance, the QRS width pulse does not begin until the middle of the R-pulse. The resultant composite, while in error, nevertheless is found to have a useful representation of the type of signal which was received and can be usefully formed into a template.

Signal 228 illustrates a condition in which a preliminary pulse of duration less than the short noise reject circuit leads to a condition where the initial QRS with the signal is terminated upon the first slope change and the initial portion of the wave 228 is ignored. The second portion of the wave initiates a normal circuit responses as indicated by the associated wave forms.

Reference is now made to FIG. 2 which shows the general form of the computer 11 of the present invention for performing the data template making template storage and composite-template/condition comparison steps of the present invention. In general, the computer receives the QRS composite from the generator or convertor 10 and completes the composite signature by template/condition match or operator classification. The computer adds tolerances to newly-classified composites to form template and stores the same in an appropriate storage location or bin for Normal, SVE, VE or unknown for future reference. The computer includes a high-speed 6502 microprocessor 230 using a 4118 Read Only Memory (ROM) 234 to contain its program instructions and fixed tables. A programable 2716 Random Access Memory (EPROM) 232 is provided for scratch pad data buffers and data tabs. The Microprocessor 230 communicates with 6522 Interface Adaptors or I/O devices 236–242 to provide access and timing functions.

The principal features and layout of the arrhythmic computer are shown in FIG. 2. The principal component descriptions and sources for the computer are:

(1) Microprocessor/CPU 230—Syp 6502B available from Synertek, Inc. of Santa Clara, Calif.
(2) EPROM 2K ×8 232—MK 2716T-6—Available from Mostek, Inc. of Carrollton, Tex.
(3) RAM 4K ×8 234—MK 4118-2—Available from Mostek, Inc. of Carrollton, Tex.
(4) I/0 Adaptors 236–242—Syp 6522A Available from Synertek of Santa Clara, Calif.

The power up logic provides the master reset to the 6502 CPU, I/O devices and ECG event counter logic. A 4 MHz crystal oscillator is counted down to provide 2 MHz clock pulses to the 6502. Address, data, and read/write lines and busses interconnect the PROM, RAM, and I/O devices with each other and the CPU. I/O devices 236, 238 are connected to the output of the composite generator 116 through line 244. An output signal from I/O 230 is connected to the tape playback unit 9 on line 235 to stop the tape when a no-match condition is present and tape speed and status (new data) signals are available on line 236 connected between the playback unit control 40 and I/O 230. Operator classification inputs from controller 40A and learn-/analyze mode selections are connected to I/O 240 on line 237. Event pulses from I/O 242 are sent to counter logic 240 which counts and displays the events.

Figure 8B:
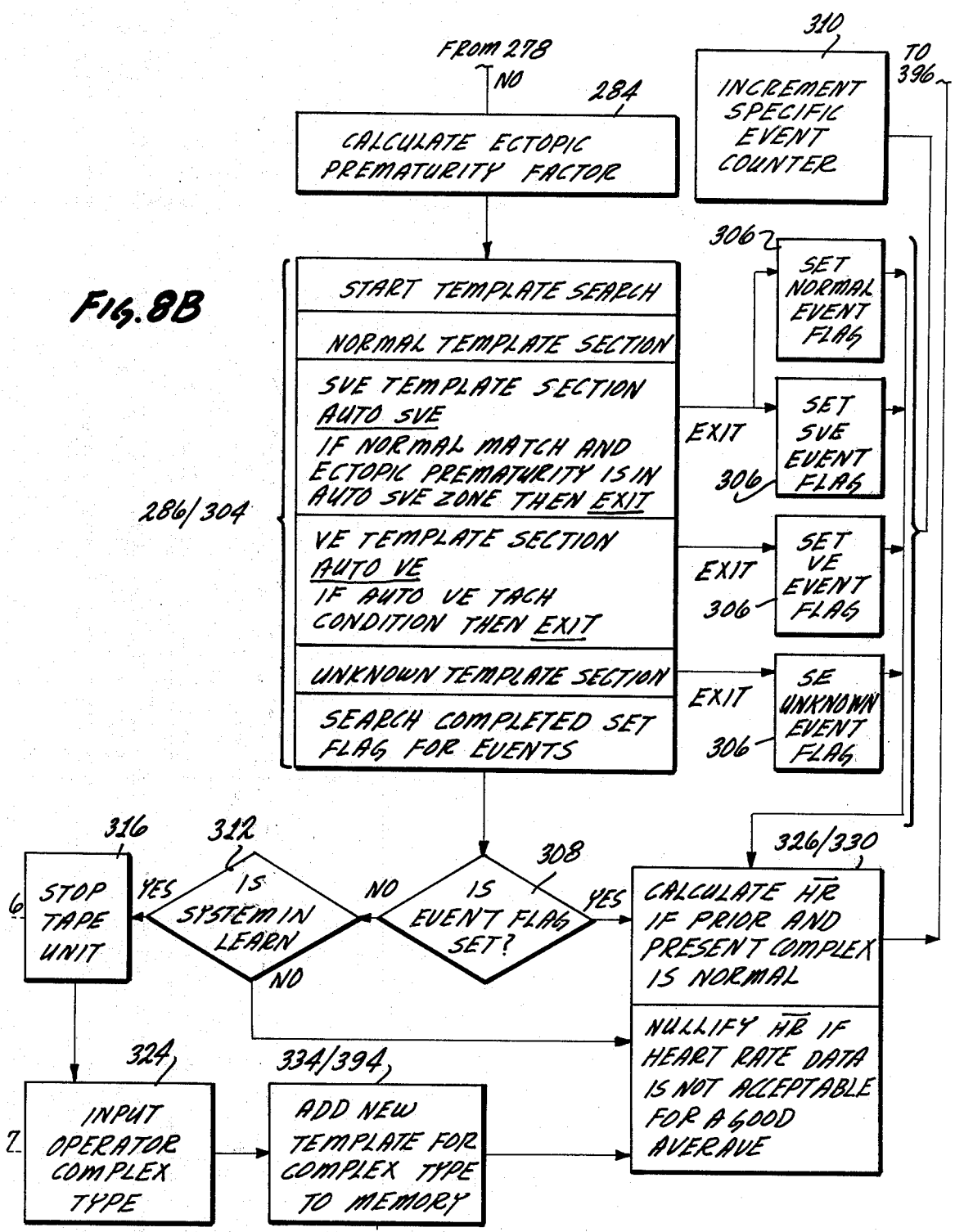

A simplified flow diagram of the logic for controlling the computer 11 is given in FIGS. 8A and 8B. A detailed flow diagram of the logic is given in FIGS. 9A, 9B, 9C. In each diagram the various decision and instruction blocks have been given the same numerical designations for ease of reference. While not deemed necessary for a complete and sufficient disclosure, a complete and detailed computer program for carrying out this portion of the method and for implementing the computer apparatus portion of the present invention is nevertheless given by Appendix I, appended hereto and incorporated herein by reference, and a copy of which is avialable for inspection at the U.S. Patent Office, Arlington, Va.

Reference is made to both FIGS. 8 and 9 taken together and serve to explain the principle decision and instruction blocks.

256/262 fetches new data and measures R-R interval.
258 outputs event results of last processed composite to computer display logic 240
264 classifies composites as artifact whenever
 (a) Slope crossings are 0–1
 (b) Slope crossings are greater than 5 or
 (c) QRS width is less than 12 milliseconds
 In part this duplicates the function of some of the circuitry of the convertor.
326–330, 346 calculates heart rate average if incoming complex is normal. Heart rate range is 35–240 BPM.

The average heart rate ($\overline{HR}$) is calculated using only R—R intervals between Normal composites. The preceding two intervals are combined to form the heartbeat average. An R—R interval is excluded whenever it approaches 2 R—R specifically whenever it is greater than 1¾ (R—R).

The HR becomes valid when there are 5 acceptable Normal R—R intervals.

The HR becomes nullified when any one of the following conditions occur:
1. Occurrence of an R—R interval greater than 3.9 seconds.
2. When the HR could not be updated for 8 consecutive heartbeats.
3. When the R—R data going into the average has large deviations when compared to the other four R—R interval making up HR. Specifically, when the ratio of the incoming R—R interval to any of the elements of HR is less than ½ or greater than 2.
4. When an artifact composite is detected.

Figure 10:
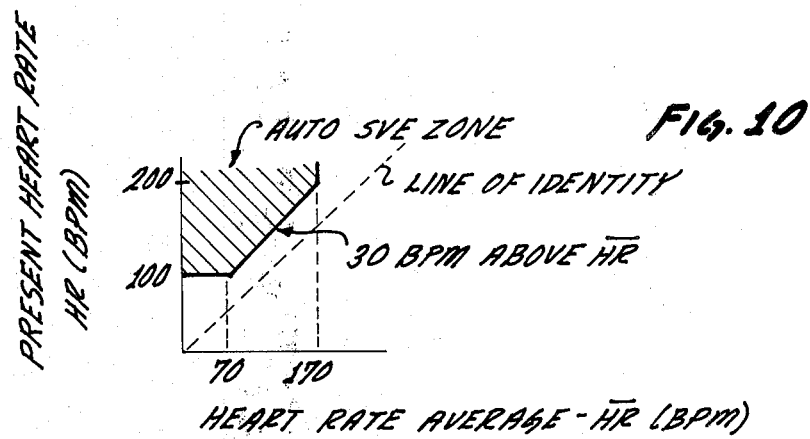
FIG. 10 is a graph of the ectopic prematurity condition for determining automatically classified supraventricular beats whenever the instantaneous heart rate suddenly escalates.

284—An ectopic prematurity factor is calculated to use in determining an auto SVE condition. It is taken by combining the HR average with the current HR which is then compared with a lock up table of values which correspond to auto SVE zone. FIG. 10 is a graph showing the zone based on the conditions HR is greater than 100 and HR is greater than 30 beats above $\overline{HR}$.

286-304 include the main decision blocks for carrying out composite comparison in accordance with the present invention.

286 compares the incoming composite with templates stored in the Normal bin of memory

290 Compares the Yes results of 286 against the prematurity condition and automatically gives an SVE output when satisfied. If the condition is not satisfied the Normal output classification is given.

292 Classifies the not Normal composites as auto VE whenever the current HR is in excess of 100 BPM and the 4 immediately-previous composites have been classified as VE.

294-298,302 are the respective decision blocks for classifying SVE ectopic, VE ectopic and unknown ectopic events based on a comparison of the incoming composite with templates stored in the respective SVE, VE and unknown bins of memory.

306 the respective outputs of the decision matrix are used to set appropriate event flags as Normal, SVE, VE and unknown.

304, 310 decision branch, if event flag set system proceeds to implement event counters and to increment event totals and HR computation:

326-330, if event flag not set system proceeds with auto Stop, complex display 316 and operator classification 324

314-310 generates Stop command when event flag not set (indicating no-match of conditions or templates) his actuates Stop command and display current complex modes of operation of playback unit and enables operator classification to proceed.

334,354,368,382 are decision blocks for accepting one operator classification. Each of these blocks controls one of instruction blocks

Figure 11:
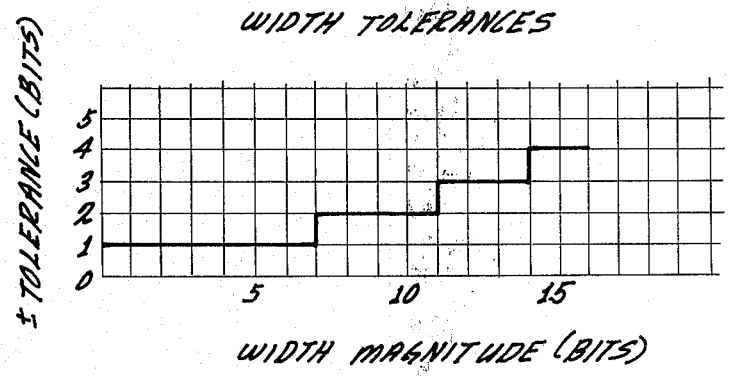
FIG. 11 is a graph showing the tolerance (±) values added to the QRS width composite measurement to derive corresponding template values.
Figure 12:
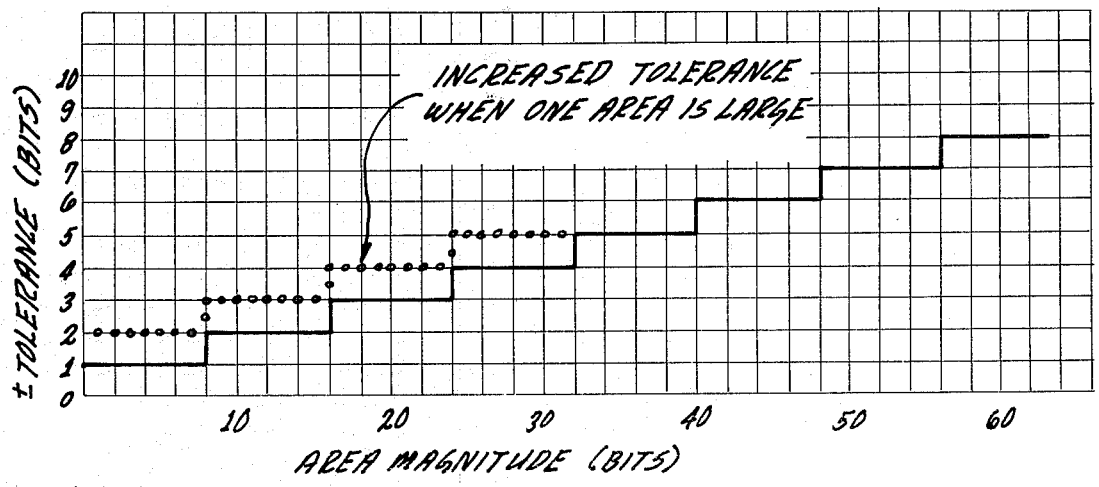
FIG. 12 is a graph showing the tolerance (±) values added to the integrated QRS area composite measurements to derive corresponding template values.

340,358,372,386 to generate a new template together with tolerances for each newly classified composite. The tolerances are scaled up in proportion to the strength and duration of the composite received. The width tolerances are given with FIG. 11 where measurements are given in bits (1 bit equals 12 milliseconds) and are added and subtracted from the composites to give template range. The area tolerances are given in FIG. 12 in bits where one bit is equal to 5 µV sec. This tolerance is also added and subtracted from the composite to give template range. The dotted lines in FIG. 12 show a portion of the graph in which the tolerance used on small areas is increased by one bit if one of the area measurements is larger than 32 bits. No tolerances are given to slope or R sign data words.

350,366,380,392 are enable instruction blocks for activating the counter and incrementing display circuits 5 in correspondence to each classified event.

The foregoing description and flow diagrams encompass both the learn and the analyze mode of operation of the present invention. In analyse mode unmatched composites do not cause the tape to stop but rather activate a scan-by in which only the heartbeat is recorded.

While the present invention is carried out with a suitably programmed microcomputer, it should be understood that the same could be carried out by building a special purpose, hard wired computer for carrying out the same tasks, specifically for carrying out the computational steps set forth in the flow diagrams of FIGS. 8 and 9. In addition, while preferred microcomputer components have been given together with appropriate instructions, it should be appreciated that other computers and peripherals could be substituted without departing from the teachings of the present invention. While the present invention has employed certain selected ECG parameters, others may be employed or substituted such as amplitude, either measured from baseline or peak to peak, aspect ratio, width of second part of bipolar complexes, rate of change of the upstroke and/or downstroke of the R-wave or others. Thus, the invention should not be taken as limiting in this sense but rather that a set of parameters has been selected by way of one suitable example. While the invention as explained herein indicates the use of both a learn mode and an analyze mode of operation and scanning, it should be pointed out that it is possible to analyze the tape in a single run since it has been found in practice that the resulting data will only differ from the accuracy of the learn analysis by a small fraction. Accordingly, the scope of this invention is to be taken solely by reference to the accompanying claims when interpreted in the light of the foregoing detailed description.

What is claimed is:

1. In a method for the analysis of a tape recording of ECG signals for normal and arrhythmic events, the steps of scanning the tape recording at high speed to create an electrical signal comprising a succession of complexes representing successive heart beats, generating composites comprising a plurality of digital words which represent measured parameters characterizing each complex, comparing each successive composite with a plurality of known templates or conditions based on prior classifications of composites of the same tape recording and outputting an event signal if a match between a composite and a template or a condition is found, counting event signals corresponding to specific normal or arrhythmic events, and continuing to scan the tape until a no-match is found between the composite and any template or condition, stopping the scan and presenting a CRT analog display of the complex corresponding to said unmatched composite, classifying the complex, forming and storing an additional template based on the classification, incrementing the count of event signals according to the classification and continuing to scan the tape to completion.

2. The method as in claim 1 in which the step of generating digital words includes synthesizing a digital word for each selected parameter of the complex selected from among QRS width, R-sign, amplitude, pulse, positive area, negative area, and number of slope changes.

3. The method as in claim 2 in which the step of making templates from composites includes adding tolerances to the composite digital words.

4. The method as in claim 3 in which the digital words to which tolerances are added are those relating to positive area measurement, negative area measurement and QRS width.

5. The method as in claim 1 further in which the step of making the templates from composites includes adding tolerances to the composite digital words.

6. The method as in claim 1 in which the step of forming templates includes the step of creating a respective memory location bin for template classifications designated as normal, VE, SVE, and unknown.

7. The method as in claim 1 further including the step of rescanning the tape recording a second time and displaying a count of selected matched events for improved accuracy over said first scan.

8. A method as in claim 7 in which said selected events include total heart beats, VE, SVE, and unknown occurrences.

9. The method as in claim 1 in which the step comparing with known templates includes classifying the templates as normal, VE, SVE, or unknown.

10. The method as in claim 1 further including the step of measuring instantaneous and average heart rate and using the same in combination with template classification to form a condition for subsequent composite classification.

11. The method as in claim 10 in which the template classifications include normal, SVE, VE, and unknown.

12. The method as in claim 11 further including the step of automatically classifying a composite SVE whenever a composite match is normal and an ectopic prematurity condition is simultaneously present based on the instantaneous and average heart rate, and subsequently incrementing SVE counts whenever such condition is present.

13. The method as in claim 11 further including the step of automatically classifying a composite VE whenever a composite template match is not normal and a prematurity condition is satisfied based on instantaneous heart rate and the number of immediately previous VE classifications, and incrementing the VE counts accordingly.

14. The method as in claim 1 in which the high-speed scanning step is carried out at from 60, 120 or 240 times real time.

15. A method as in claim 1 further including the step of displaying successive complexes during said high-speed scanning step as a superimposed AVSEP display.

16. A method as in claim 1 in which the display of complexes corresponding to unmatched composites is a repeated time lapse display of an interval of a tape recording containing said unmatched complex.

17. A method as in claim 1 in which displaying of the unmatched complex includes the steps of storing a selected interval of ECG signal from the tape recording in a memory, and replaying that interval repeatedly on an oscilloscope.

18. The method of claim 17 in which the step of continuing the scanning of the tape includes the step of measuring the time occurrence of each unmatched complex on the tape recording and beginning said continuation of scan step at a preset time later in said recording and immediately following the said unmatched complex.

19. A method for the high-speed analysis of ECG data wherein said data is collected from a patient in actual time and stored for subsequent processing, and wherein said analysis includes recognition of at least VE beats and SVE beats, comprising the steps of:
measuring preselected parameters of a first plurality of normal beats from the stored patient ECG data and separately storing the same to form a first template bin composed of sets of preselected parameters of a series of normal beats,
measuring preselected parameters of a second plurality of VE beats from patient ECG data and separately storing the same to form a second template bin composed of sets of preselected parameters of a series of VE beats,
measuring preselected parameters of a third plurality of SVE beats from the stored patient ECG data and separately storing the same to form a third template bin composed of sets of preselected parameters of a series of SVE beats,
comparing the preselected parameters of each successive beat with the preselected parameters of each template in said first template bin to determine which of said beats is normal and not-normal,
comparing the normal beats with a prematurity condition to derive an (Auto) SVE event signal whenever the condition is satisfied and a normal event signal whenever the condition is not satisfied,
comparing the not-normal beats to pre-existing VE and to heart rate data conditions to determine which are auto VE beats, outputting a VE signal whenever said conditions are satisfied,
comparing the remaining not-normal beats with the preselected parameters of each of the series of SVE templates in said third template bin to determine which are SVE beats, and outputting an SVE event signal whenever a match is found,
comparing the remaining not-normal beats in said data with the selected parameters of the series of VE templates in said second template bin to determine which are VE beats, and outputting a VE signal whenever a match is found,
wherein said preselected parameters for each beat include at least QRS pulse width, plus area of the R wave, minus area of the S wave.

20. The method of claim 19 wherein said first, second and third template bins are characterized by upper and lower bounds for each of said preselected parameters as determined by said steps of measuring for said first, second and third plurality of beats respectively, said upper and lower bounds for each said parameters being the maximum and minimum values of said parameters corresponding to said first, second and third pluralities of beats corresponding to said first, second and third templates.

21. The method of claim 20 wherein said first, second and third pluralities of beats include said successive beats if said successive beats are characterized by values of said preselected parameters outside said upper and lower bounds pre-established by said first, second and third pluralities of beats; and further comprising the step of:

re-establishing said upper and lower bounds for each parameter by including said value of said successive beats outside said pre-established upper and lower bounds.

22. In an apparatus for analyzing ECG tape recordings for arrhythmic events, means for scanning recordings at high speed and for creating an electrical signal of successive ECG complexes therefrom, means for receiving said signal and for converting each complex into a composite of digital words which represent measured parameters representing the same, means for making and storing a plurality of classified templates corresponding to previously-identified composites, means operative during said scan for comparing each new composite with said stored templates to determine if a match is found, means for stopping said scanning means and for displaying each complex corresponding to an unmatched composite in a stable view for operator classification, means responsive to operator classification for generating a new template for delivery to said storage means, means for counting and displaying a total of matched and classified events of said scanned tape recording.

23. Apparatus as in claim 22 in which said means for converting each complex is an analog computer and further in which said means for making and storing templates is a digital computer.

24. Apparatus as in claim 22 in which said means for converting each complex includes trigger means for sensing when a complex of predetermined strength and rise time is present, means responsive to said trigger means for measuring the QRS width of the complex from the inception of the initial R-wave to the nadir of the S-wave and for generating a digital representation thereof.

25. Apparatus as in claim 24 further including means responsive to the trigger means for measuring the magnitude of the time integral of the amplitude of the R-wave of the complex and for generating a digital representation thereof.

26. Apparatus as in claim 24 further including means responsive to said trigger means for measuring whether the initial R-wave of each complex is positive or negative and for generating a digital representation thereof.

27. Apparatus as in claim 24 further including means responsive to said trigger means for counting the number of slope changes of said video signal during said QRS width interval and for generating a digital representation thereof.

28. Apparatus as in claim 22 in which said means for storing templates includes a bin for each classification of complex including normal, SVE, VE and unknown.

29. Apparatus as in claim 28 in which said means for storing templates is a digital computer memory.

30. Apparatus as in claim 29 in which said means for comparing templates and composites is a digital computer including memory programmed to provide a means for each classification of complex and template including normal, SVE, VE, and unknown and further programmed to provide means for comparing each composite against stored templates in a decision matrix including: normal, auto SVE, if normal and premature; auto VE, if following a series of VE beats above a predetermined heart rate; SVE; VE, and unknown, and for providing an output signal for respective events, means for counting said classified events.

31. Apparatus as in claim 22, said means responsive to operator classification, includes a hand-held controller having a plurality of classification indices thereon responsive to operator touch to effect classification selection and to initiate restart of said scanning means.

32. Apparatus as in claim 22 further including means for computing the R—R interval between successive normal heart beats and for computing ectopic prematurity, average and instantaneous heart rate therefrom.

33. Apparatus as in claim 22 further including means responsive to operator control for generating a printout of the displayed complex.

34. An apparatus for analyzing extended tape recordings of a patient's ECG activities for the presence of normal and ectopic beats, a tape playback transport including playback head means responsive to said tape recording for generating an analog electrical signal therefrom, means for supporting said tape recording for high-speed scan movement past said head so that successive complexes are detected, a display oscilloscope, means for generating AVSEP display on said oscillocope of said complexes during said high-speed scan of said tape recording, memory means for storing a selected interval of the signal on said tape recording for subsequent display in real time, means operative during said scan and responsive to said electrical signals for measuring preselected parameters of each of said complexes selected from among the QRS width or R-sign, slope, plus area, minus area, and amplitude, and for generating a digital composite of each complex therefrom, computer means for accepting each digital composite, and including memory means for forming template bins corresponding to patient data classified as normal, SVE, VE, and unknown events, such computer programmed to compare the data stored in template bins with each received composite and to generate an appropriate event whenever a match occurs, means responsive to a no-match condition for stopping the playback transporter causing the transfer of said oscilloscope to display at least a portion of the ECG interval from said memory means and including the unmatched complex therein, means for said computer further programmed to respond to operator input classification of said displayed complex to generate a new template for storage in a respective bin in said memory and for generating an event signal corresponding to such classification, counting means for totaling said matched and classified event signals.

35. A method for the high-speed analysis of ECG data wherein said data is collected from a patient in actual time and stored for subsequent processing, and wherein said analysis includes recognition of at least VE beats and SVE beats, comprising the steps of:

measuring preselected parameters of a first plurality of normal beats from the stored patient ECG data and separately storing the same to form a first template bin composed of upper and lower bounds of preselected parameters of a series of normal beats, measuring preselected parameters of a second plurality of VE beats from patient ECG data and separately storing the same to form a second template bin composed of upper and lower bounds of preselected parameters of a series of VE beats, measuring preselected parameters of a third plurality of SVE beats from the stored patient ECG data and separately storing the same to form a third template bin composed of upper and lower bounds of preselected parameters of a series of SVE beats, comparing the preselected parameters of each successive beat with the preselected parameters of each template in said first template bin to determine which of said beats is normal and not-normal, comparing the normal beats with a prematurity condition to derive an (Auto) SVE event signal whenever the condition is satisfied and a normal event signal whenever the condition is not satisfied, comparing the not-normal beats to pre-existing VE and to heart rate data conditions to determine which are auto VE beats, outputting a VE signal whenever said conditions are satisfied, comparing the remaining not-normal beats with the preselected parameters of each of the series of SVE templates in said third template bin to determine which are SVE beats, and outputting an SVE event signal whenever a match is found, comparing the remaining not-normal beats in said data with the selected parameters of the series of VE templates in said second template bin to determine which are VE beats, and outputting a VE signal whenever a match is found, and re-establishing each said upper and lower bound corresponding to said first, second and third pluralities of beats for each said parameter when a value of said parameter for a corresponding successive beat is outside said initially established upper and lower bounds, said successive beat corresponding to a normal beat, VE beat, or SVE beat.

36. In a method for the analysis of a recording of ECG signals for normal and arrhythmic events, the steps of:

scanning the recording at high speed to create an electrical signal comprising a succession of complexes representing successive heartbeats;

generating composites comprising a plurality of digital words which represent measured parameters characterizing each complex, each digital word having a tolerance associated therewith;

comparing each successive composite with a plurality of known templates based on said previously generated composites of the same tape recording; and outputting an event signal if a match within said tolerances between a composite and a template is found, whereby classification of said complexes is simplified by including all heartbeats as matched when said heartbeat falls within a predetermined tolerance of said templates.

37. The method as in claim 36 in which the digital words to which tolerances are added are those relating to positive area measurement, negative area measurement and QRS width.

38. In a method for the analysis in an automated apparatus of a recording of ECG signals for normal and arrhythmic events, the steps of:

scanning the recording at high speed to create an electrical signal comprising a succession of complexes representing successive heart beats;

generating composites comprising a plurality of digital words which represent measured parameters characterizing each complex;

measuring instantaneous and average heart rate and using the same in combination with template classification to form a condition for subsequent composite classification;

comparing each successive composite with a plurality of known templates or conditions based on said previously generated composites of the same recording;

automatically classifying a composite as auto VE whenever a composite template match is not normal and a prematurity condition is satisfied based on instantaneous heart rate and the number of immediately previous VE classifications; and outputting an event signal if a match between a composite and a template or a condition if found whereby auto VE tachycardia is classified in an accelerated mode without stopping the analysis for nonautomated classification of each heartbeat.

39. An improvement in an apparatus for analyzing ECG recordings for arrhythmic events, comprising:

means for scanning recordings at high speed and for creating an electrical signal of successive ECG complexes therefrom;

means for receiving said signal and for converting each complex into a composite of digital words which represent measured parameters representing the same wherein said means for converting each complex is an analog computer for generating at least some of said measured parameters; and means for making and storing a plurality of classified templates corresponding to previously-identified composites, wherein said means for making and storing templates is a digital computer.

40. The improvement of claim 39 wherein said analog computer integrates selected portions of said ECG complexes and wherein said digital computer compares said templates to said ECG complexes.

* * * * *